US008324359B1

(12) United States Patent
Lugade et al.

(10) Patent No.: US 8,324,359 B1
(45) Date of Patent: Dec. 4, 2012

(54) OXOCARBONAMIDE PEPTIDE NUCLEIC ACIDS AND METHODS OF USING SAME

(75) Inventors: Ananda G. Lugade, Austin, TX (US); James W. Jacobson, Leander, TX (US)

(73) Assignee: Luminex Corporation, Austin, TX (US)

(*) Notice: Subject to any disclaimer, the term of this patent is extended or adjusted under 35 U.S.C. 154(b) by 1405 days.

(21) Appl. No.: 11/947,705

(22) Filed: Nov. 29, 2007

Related U.S. Application Data

(60) Provisional application No. 60/868,514, filed on Dec. 4, 2006.

(51) Int. Cl.
C07H 21/00 (2006.01)
C12Q 1/68 (2006.01)
(52) U.S. Cl. .............. 536/23.1; 435/6; 422/60
(58) Field of Classification Search ............... 536/23.1; 435/6; 422/60
See application file for complete search history.

(56) References Cited

U.S. PATENT DOCUMENTS

| | | | | |
|---|---|---|---|---|
| 5,539,082 | A | 7/1996 | Nielsen et al. | 530/300 |
| 5,714,331 | A | 2/1998 | Buchardt et al. | 435/6 |
| 5,719,262 | A | 2/1998 | Buchardt et al. | 530/300 |
| 5,736,336 | A | 4/1998 | Buchardt et al. | 435/6 |
| 5,766,855 | A | 6/1998 | Buchardt et al. | 435/6 |
| 5,773,571 | A | 6/1998 | Nielsen et al. | 530/300 |
| 5,786,461 | A | 7/1998 | Buchardt et al. | 536/18.7 |
| 5,891,625 | A | 4/1999 | Buchardt et al. | 435/6 |
| 5,981,180 | A | 11/1999 | Chandler et al. | 435/6 |
| 6,057,107 | A | 5/2000 | Fulton | 435/6 |

FOREIGN PATENT DOCUMENTS

| | | |
|---|---|---|
| EP | 0646596 | 4/1995 |
| WO | WO 92/20702 | 11/1992 |
| WO | WO 98/16550 | 4/1998 |

OTHER PUBLICATIONS

PCT International Search Report and Written Opinion issued in International Application No. PCT/US2007/085927, dated Apr. 23, 2008.
Ambros et al., "A uniform system for microRNA annotation," *RNA*, 9:277-279, 2003.
Calin et al., "Frequent deletions and down-regulation of micro-RNA genes miR15 and miR16 at 13q14 in chronic lymphocytic leukemia," *Proc. Natl. Acad. Sci. USA*, 99:15524-15529, 2002.
Egholm et al., "PNA hybridizes to complementary oligonucleotides obeying the Watson-Crick hydrogen-bonding rules," *Nature*, 365(6446):566-568, 1993.
Fire et al., "Potent and specific genetic interference by double-stranded RNA in *Caenorhabditis elegans*," *Nature*, 391:806-811, 1998.
Fujii et al., "Hybridization properties of nucleic acid analogs containing beta-aminoalanine modified with nucleobases," *Chem. Commun.*, 717-718, 1998.
Girault et al., "Use of Morpholinonucleosides to Conjugate Oxidized DNA Bases to Proteins," *Bioconj. Chem.*, 7:445-450, 1996.

(Continued)

*Primary Examiner* — Jezia Riley
(74) *Attorney, Agent, or Firm* — Fulbright & Jaworski L.L.P.

(57) ABSTRACT

The present invention concerns oxocarbonamide peptide nucleic acids (OxoPNAs). OxoPNAs provide increased stability, sensitivity, and specificity as compared to their natural DNA and RNA counterparts. The OxoPNA molecules of the present invention may be employed in a wide range of applications, particularly in applications involving hybridization. For example, OxoPNA probes may be employed for the detection and functional analysis of nucleic acid molecules, including miRNAs and other non-coding RNAs.

25 Claims, 9 Drawing Sheets

PG = Protecting Group such as Boc or Fmoc
R = H or lower alkyl

OTHER PUBLICATIONS

Grad et al., "Computational and experimental identification of *C. elegans* microRNAs," *Mol. Cell*, 11:1253-1263, 2003.

Grishok et al., "Genes and Mechanisms Related to RNA Interference Regulate Expression of the Small Temporal RNAs that Control *C. elegans* Developmental Timing," *Cell*, 106:23-34, 2001.

Howarth and Wakelin, "alpha-PNA: A Novel Peptide Nucleic Acid Analogue of DNA," *J. Org. Chem.*, 62:5441-5450, 1997.

Hutvagner and Zamore, "A microRNA in a multiple-turnover RNAi enzyme complex," *Science*, 297:2056-2060, 2002.

Hyrup and Nielsen, "Peptide Nucleic Acids (PNA): Synthesis, Properties and Potential Applications," *Bioorganic & Medicinal Chemistry*, 4:5-23, 1996.

Ke et al., "MicroRNAs: key participants in gene regulatory networks," *Curr. Opin. Chem. Biol.*, 7:516-523, 2003.

Koshkin and Dunford, "Reaction of prostaglandin endoperoxide synthase with cis,cis-eicosa-11,14-dienoic acid," *J. Biol. Chem.*, 273(11):6046-6049, 1998.

Koshkin and Wengel, "Synthesis of Novel 2',3'-Linked Bicyclic Thymine Ribonucleosides," *J. Org. Chem.*, 63(8):2778-2781, 1998.

Krichevsky et al., "A microRNA array reveals extensive regulation of microRNAs during brain development," *RNA*, 9:1274-1281, 2003.

Lagos-Quintana et al., "Identification of Novel Genes Coding for Small Expressed RNAs," *Science*, 294:853-858, 2001.

Lau et al., "An Abundant Class of Tiny RNAs with Probable Regulatory Roles in *Caenorhabditis elegans*," *Science*, 294:858-862, 2001.

Lee et al., "The *C. elegans* Heterochronic Gene lin-4 Encodes Small RNAs with Antisense Complementarity to lin-14," *Cell*, 75:843-854, 1993.

Lipardi et al., "RNAi as Random Degradative PCR: siRNA Primers Convert mRNA into dsRNAs that are Degraded to Generate New siRNAs," *Cell*, 107:297-307, 2001.

Liu et al., "An oligonucleotide microchip for genome-wide microRNA profiling in human and mouse tissues," *Proc. Natl. Acad. Sci, USA*, 101:9740-9744, 2004.

Lundin et al., "Increased stability and specificity through combined hybridization of peptide nucleic acid (PNA) and locked nucleic acid (LNA) to supercoiled plasmids for PNA-anchored "Bioplex" formation," *Biomolecular Engineering*, 22:185-192, 2005.

McCairn et al., "Solid-Phase PNA Synthesis and in Situ Scintillation Proximity Assay for the Detection of PNA-DNA Hybridization," *J. Combinatorial Chem.*, 8(1):1-3, 2006.

Nelson et al., "The microRNA world: small is mighty," *TIBS*, 28:534-540, 2003.

Ng and Bergstrom, "Alternative nucleic acid analogues for programmable assembly: hybridization of LNA to PNA," *Nano Letters*, 5:107-111, 2005.

Nykanen et al., "ATP Requirements and Small Interfering RNA Structure in the RNA Interference. Pathway," *Cell*, 107:309-321, 2001.

Paushkin et al., "The SMN complex, an assemblyosome of ribonucleoproteins," *Curr. Opin. Cell Biol.*, 14:305-312, 2002.

Pfeffer et al., In: *Cloning of Small RNA Molecules in Current Protocols in Molecular Biology*, Ausubel et al. (Eds), Ch. 26.4.1-26.4.18, Wiley Interscience, NY, 2003.

Porter et al., "Squaric Acid Derivatives as VLA-4 Integrin Antagonists," *Bioorganic Med. Chem. Ltrs.*, 12:1051-1054, 2002.

Poy et al., "A pancreatic islet-specific microRNA regulates insulin secretion," *Nature*, 432:226-230, 2004.

Reinhart et al., "MicroRNAs in plants," *Genes Dev.*, 16:1616-1626, 2002.

Roberts, "MicroRNA expression profiling on arrays enhanced with locked nucleic acids," *Nature Methods*, iii-iv, 2006.

Sato et al., "Squaryl group as a new mimic of phosphate group in modified oligodeoxynucleotides: synthesis and properties of new oligodeoxynucleotide analogues containing an internucleotidic squaryldiamide linkage," *J. Am. Chem. Soc.*, 124:12715-12724, 2002.

Sato et al., "Synthesis and properties of a new oligonucleotide analogue containing an internucleotide squaryl amide linkage," *Nucleic Acids Res. Suppl.*, (1):121-122, 2001.

Schmittgen et al., "A high-throughput method to monitor the expression of microRNA precursors," *Nucleic Acids Res.*, 32:e43, 2004.

Seio et al., "Synthesis and Properties of New Nucleotide Analogues Possessing Squaramide Moieties as New Phosphate Isosters," *European J. Org. Chem.*, 24:5163-5170, 2005.

Thomson et al., "A custom microarray platform for analysis of microRNA gene expression," *Nature Methods*, 1:1-7, 2004.

Valoczi et al., "Sensitive and specific detection of microRNAs by northern blot analysis using LNA-modified oligonucleotide probes," *Nuc. Acids Res.*, 32(22):e175, 2004.

Wahlestedt et al., "Potent and nontoxic antisense oligonucleotides containing locked nucleic acids," *Proc. Natl. Acad. Sci. USA*, 97(10):5633-5638, 2000.

Weiler et al., "Anti-miRNA oligonucleotides (AMOs): ammunition to target miRNAs implicated in human disease?," *Gene Therapy*, 13:496-502, 2006.

Zeng and Cullen, "Sequence requirements for micro RNA processing and function in human cells," *RNA*, 9:112-123, 2003.

Zhang et al., "Human Dicer preferentially cleaves dsRNAs at their termini without a requirement for ATP," *EMBO J.*, 21:5875-5885, 2002.

Deltic acid

Thio-deltic acid

Croconic acid

Thio-Croconic acid

Rhodizonic acid

Thio-Rhodizonic acid

Squaric acid

Thio-Squaric acid

Abasic Monomers

R1 and R2 are independently selected from the group consisting of H, $CH_2NH_2$, $(CH_2)_{(1-10)}HN_2$, $(CH_2)_2(OCH_2CH_2)_{(1-10)}NH_2$, and $(CH_2)_2(OCH_2CH_2)_{(1-10)}CO_2H$, $(CH_2)_{(1-10)}$

Reactive Derivatives

X = halogen
R = lower alkyl

PG = Protecting Group such as Boc or Fmoc
R = H or lower alkyl

OXOCARBONAMIDE PEPTIDE NUCLEIC ACIDS AND METHODS OF USING SAME

This application claims priority to U.S. Application No. 60/868,514, filed on Dec. 4, 2006, the entire disclosure of which is incorporated by reference.

BACKGROUND OF THE INVENTION

1. Field of the Invention

The present invention relates generally to nucleic acid probes useful in the detection and analysis of target nucleic acid sequences. More particularly, the present invention concerns nucleic acid probes wherein naturally occurring nucleobases or other nucleobase-binding moieties are covalently bound to an oxocarbonamide containing peptide backbone. In certain aspects, the present invention concerns methods employing nucleic acid probes in the detection and analysis of target nucleic acid sequences including, for example, mRNAs, miRNAs, and siRNAs.

2. Description of Related Art

A large number of small, non-coding RNAs have been identified and designated as microRNAs (miRNAs) (Ke et al., 2003). miRNAs have been shown to regulate gene expression at many levels, representing a novel gene regulatory mechanism. Understanding this RNA-based regulation will be useful to understand the complexity of the genome in higher eukaryotes as well as understand the complex gene regulatory networks.

miRNAs are 18-25 nucleotide (nt) RNAs that are processed from longer endogenous hairpin transcripts by the enzymes Dicer and Argonaute (Ambros et al., 2003; Grishok et al., 2001). To date more than 4160 microRNAs have been identified in mammals, birds, fish, worms, flies, plants, and viruses according to the miRNA registry database release 9.0 in October 2006, hosted by Sanger Institute, UK. Some miRNAs have multiple loci in the genome (Reinhart et al., 2002) and may be arranged in tandem clusters (Lagos-Quintana et al., 2001).

The first miRNAs to be discovered, lin-4 and let-7, base-pair incompletely to repeated elements in the 3' untranslated regions (UTRs) of other heterochrony genes, and regulate the translation directly and negatively by antisense RNA-RNA interaction (Lee et al., 1993; Reinhart et al., 2000). Some miRNAs are thought to interact with target mRNAs by limited complementary and suppressed translation as well (Lagos-Quintana et al.,. 2001; Lee and Ambros, 2001). Perfect complementarity between miRNAs and their target RNA may lead to target RNA degradation rather than inhibit translation (Hutvagner and Zamore, 2002), which suggests that the degree of complementarity determines function.

Several human diseases have been identified in which miRNAs or their processing machinery might be implicated. One such disease is spinal muscular atrophy (SMA), a pediatric neurodegenerative disease caused by reduced protein levels or loss-of-function mutations of the survival of motor neurons (SMN) gene (Paushkin et al., 2002). Another disease linked to mi/siRNAs is fragile X mental retardation (FXMR) caused by absence or mutations of the fragile X mental retardation protein (FMRP) (Nelson et al., 2003). Poy et al. (2004) concluded that miR-375 is a regulator of insulin secretion and could constitute a novel pharmacological target for the treatment of diabetes. Links between cancer and miRNAs have also been described. For example, one study determined that two different miRNA (miR15 and miR16) genes are clustered and located within the deleted minimal region of the B-cell chronic lymphocytic leukemia (B-CLL) tumor suppressor locus, and both genes are deleted or down-regulated in the majority of CLL cases (Calin et al., 2002).

RNA interference (RNAi), in which double-stranded RNA leads to the degradation of any RNA that is homologous (Fire et al., 1998), relies on a mechanism that probably evolved for protection against viral attack and mobile genetic elements. One step in the RNAi mechanism is the generation of short interfering RNAs (siRNAs), double-stranded RNAs that are about 22 nt long. The siRNAs lead to the degradation of homologous target RNA and the production of more siRNAs against the same target RNA (Lipardi et al., 2001; Zhang et al., 2002; Nykanen et al., 2001).

The involvement of short RNAs in gene regulation has resulted in high interest among researchers in the discovery of siRNAs, miRNAs, their targets and mechanism of action. However, the detection and analysis of these small RNAs is not trivial. The size and often low level of expression of miRNAs require the use of sensitive analysis tools. The use of conventional quantitative real-time PCR for monitoring expression of mature miRNAs is excluded due to their small size. Most miRNA researchers use Northern blot analysis combined with polyacrylamide gels to examine expression of both the mature and pre-miRNAs (Reinhart et al., 2000; Lagos-Quintana et al., 2001; Lee and Ambros, 2001). Primer extension has also been used to detect the mature miRNA (Zeng and Cullen, 2003). Disadvantages of all the gel-based assays (Northern blotting, primer extension, RNase protection assays etc.) for monitoring miRNA expression include low throughput and poor sensitivity. Consequently, a large amount of total RNA per sample is required for gel-based methods, which is not feasible when the cell or tissue source is limited.

Microarrays are an alternative to Northern blot analysis for analyzing miRNA expression. Krichevsky et al. (2003) used cDNA microarrays to monitor the expression of miRNAs during neuronal development; however, the mature miRNAs had to be separated from the miRNA precursors using micro concentrators prior to microarray hybridization. Liu et al (2004) developed a microarray for expression profiling of 245 human and mouse miRNAs using 40-mer DNA oligonucleotide capture probes. Thomson et al. (2004) described the development of a oligonucleotide microarray platform for expression profiling of 124 mammalian miRNAs using oligonucleotide capture probes complementary to the mature microRNAs.

Although microarrays can provide high throughput, the disadvantages of DNA-based oligonucleotide arrays may include: the requirement of high concentrations of labeled input target RNA for efficient hybridization and signal generation, low sensitivity for rare and low-abundant miRNAs, and the necessity for post-array validation using more sensitive assays.

A PCR-based approach has also been used to determine the expression levels of mature miRNAs (Grad et al., 2003). However, this method is cumbersome for routine miRNA expression profiling, since it involves gel isolation of small RNAs and ligation to linker oligonucleotides. Schmittgen et al. (2004) described an alternative method to Northern blot analysis, in which real-time PCR assays were used to quantify the expression of miRNA precursors. The disadvantage of this method, however, is that it only allows quantification of the precursor miRNAs, which does not necessarily reflect the expression levels of mature miRNAs.

Many limitations of DNA probes for the detection of short nucleotide targets have been overcome by using locked nucleic acid (LNA) based probes or peptide nucleic acid (PNA) based probes. The use of LNAs and PNAs in oligonucleotide probes has been shown to increase sensitivity and selectivity for small RNA targets compared to their DNA-probe counterparts (see e.g., Valoczi et al., 2004). Nevertheless, additional compositions and methods are needed to increase the sensitivity and specificity of oligonucleotide sequences for the detection and analysis of miRNAs and other small RNAs, as well as for use in disease diagnostics and for antisense-based therapies.

The present invention addresses these needs by providing novel oligonucleotide compositions for the accurate, sensitive, and specific detection and functional analysis of miRNAs and other non-coding RNAs. The compositions of the present invention will also be useful as biomarkers for disease diagnostics as well as for antisense-based intervention targeted against disease-associated miRNAs and other non-coding RNAs.

SUMMARY OF THE INVENTION

The present invention provides a novel class of compounds that bind complementary DNA and RNA strands. The compounds of the invention generally comprise ligands linked to a oxocarbon acid amide modified peptide backbone. Non-limiting examples of ligands include thymine, cytosine, adenine, guanine, uracil, inosine, 5-methylcytosine, thiouracil, bromothymine, azaadenine, or azaguanine. Representative oxocarbon acid amides ("oxocarbonamides") include deltic acid amide, thio-deltic acid amide, squaric acid amide, thio-squaric acid amide, croconic acid amide, thio-croconic acid amide, rhodizonic acid amide, and thio-rhodizonic acid amide.

In one embodiment, the present invention provides oxocarbonamide peptide nucleic acids having the formula (I):

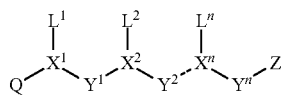

(I)

wherein:

n is at least 1;

each of $L^1$-$L^n$ is independently selected from the group consisting of heteroatom substituted aryls, naturally occurring nucleobases, non-naturally occurring nucleobases, nucleobase binding groups, hydrogen, hydroxy, ($C_1$-$C_4$)alkanoyl, aromatic moieties, and reporter ligands, wherein at least one of $L^1$-$L^n$ is a naturally occurring nucleobase, non-naturally occurring nucleobase, nucleobase binding group, or DNA intercalator;

each of $x^1$-$x^n$ is independently selected from the group consisting of $R_1NH$ and $NHR_2$, wherein $R_1$ and $R_2$ are independently selected from the group consisting of H, $CH_2NH_2$, $(CH_2)_{(1-10)}$—$NH_2$, $(CH_2)_2(OCH_2CH_2)_{(1-10)}NH_2$, $(CH_2)_2(OCH_2CH_2)_{(1-10)}CO_2H$, $(CH_2)_{(1-10)}$;

each of $Y^1$-$Y^n$ is independently selected from the group consisting of $CH_2CO$, formula (IVa), formula (IVb), formula (IVc), formula (IVd), formula (IVe), formula (IVf), formula (IVg), and formula (IVh), and where at least one Y is formula (IVa), formula (IVb), formula (IVc), formula (IVd), formula (IVe), formula (IVf), formula (IVg), and formula (IVh),

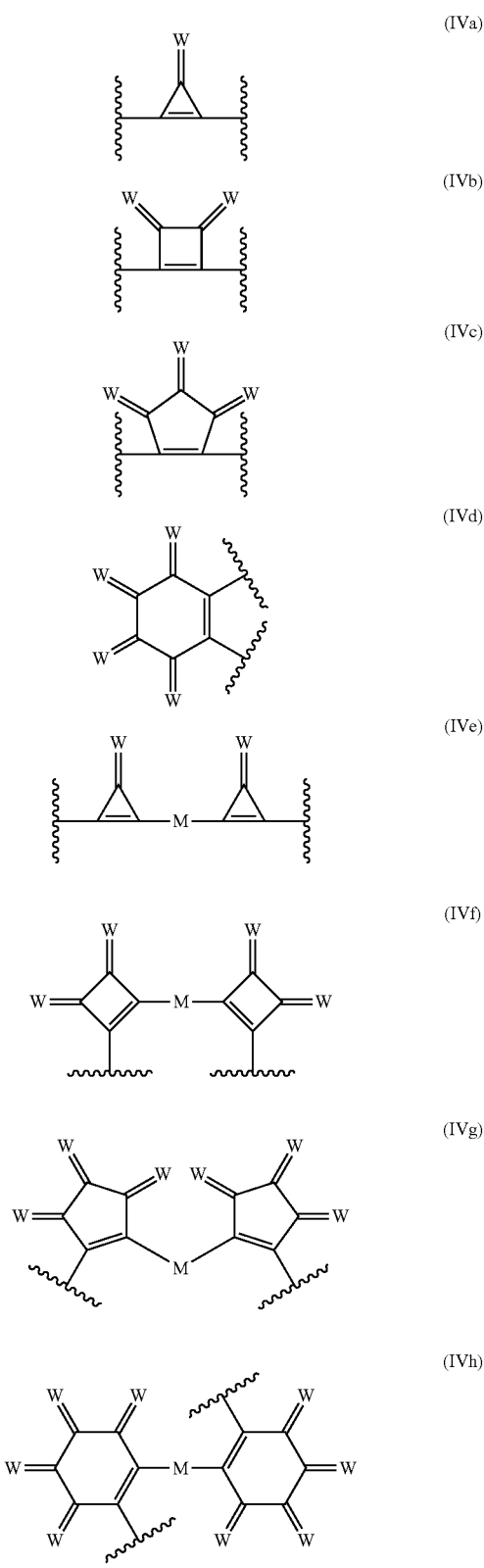

wherein each W is independently selected from the group consisting of O and S, and M is selected from the group consisting of no linker, benzene, substituted benzene, formula (IVi), and formula (IVj);

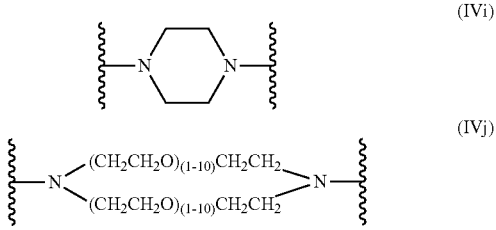

Q is selected from the group consisting of CO$_2$H, CONR'R", SO$_3$H, NH$_2$, SH, or SO$_2$NR'R" or an activated derivative of CO$_2$H or SO$_2$H; and Z is selected from the group consisting of CO$_2$H, CONR'R", SO$_3$H, NH$_2$, SH, SO$_2$NR'R", NHR"R"', or NR"'COR"", where R', R", R"', and R"" are independently selected from the group consisting of hydrogen, alkyl, amino protecting groups, reporter ligands, heteroatom substituted acyls, carboxylates, esters, alcohols, alkoxy, hydroxy alkyl, heratom substituted alkyls, carbamides, aldehydes, amines, amides, sulfur oxides, nitrogen oxides, halides, reporter ligands, intercalators, chelators, peptides, proteins, carbohydrates, lipids, steroids, oligonucleotides, and soluble and non-soluble polymers.

The substituted benzene may be substituted with, for example, alkyl, amine, substituted amine, amide, branched amine, PEG, etc.

In certain embodiments, the present invention provides oxocarbonamide peptide nucleic acids having the formula (II):

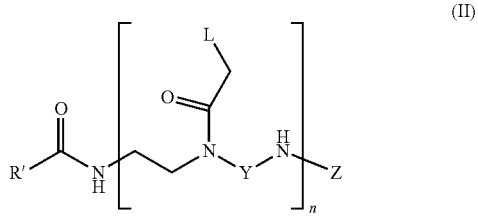

wherein:

each L is independently selected from the group consisting of heteroatom substituted aryls, naturally occurring nucleobases, non-naturally occurring nucleobases, nucleobase binding groups, hydrogen, hydroxy, (C$_1$-C$_4$)alkanoyl, aromatic moieties, and reporter ligands, wherein at least one of L$^1$-L$^n$ is a heteroatom substituted acyl, naturally occurring nucleobase, non-naturally occurring nucleobase, nucleobase binding group, or DNA intercalator;

each Y is independently selected from the group consisting of CH$_2$CO, formula (IVa), formula (IVb), formula (IVc), formula (IVd), formula (IVe), formula (IVf), formula (IVg), and formula (IVh), and where at least one Y is formula (IVa), formula (IVb), formula (IVc), formula (IVd), formula (IVe), formula (IVf), formula (IVg), and formula (IVh);

R' is selected from the group consisting of hydrogen, alkyl, amino protecting groups, reporter ligands, heteroatom substituted acyl, carboxylates, esters, alcohols, alkoxy, hydroxy alkyl, heteroatom substituted alkyl, heteroatom substituted acyl, carbamides, aldehydes, amines, amides, sulfur oxides, nitrogen oxides, halides, reporter ligands, intercalators, chelators, peptides, proteins, carbohydrates, lipids, steroids, oligonucleotides, and soluble and non-soluble polymers;

Z is selected from the group consisting of CO$_2$H, CONR'R", SO$_3$H, NH$_2$, SH, SO$_2$NR'R", NHR"R"', or NR"'COR"", where R', R", R"', and R"" are independently selected from the group consisting of hydrogen, alkyl, amino protecting groups, reporter ligands, heteroatom substituted acyl, carboxylates, esters, alcohols, alkoxy, hydroxy alkyl, heteroatom substituted alkyl, heteroatom substituted acyl, carbamides, aldehydes, amines, amides, sulfur oxides, nitrogen oxides, halides, reporter ligands, intercalators, chelators, peptides, proteins, carbohydrates, lipids, steroids, oligonucleotides, and soluble and non-soluble polymers; and n is an integer from 1 to 100.

In certain embodiments, the present invention provides an oxocarbonamide peptide nucleic acid having the formula (II):

wherein:

n is an integer from 1 to 100;

each L is independently selected from the group consisting of heteroatom substituted aryl, naturally occurring nucleobases, non-naturally occurring nucleobases, nucleobase binding groups, and DNA intercalators;

each Y is independently selected from the group consisting of CH$_2$CO, formula (IVa), formula (IVb), formula (IVc), formula (IVd), formula (IVe), formula (IVf), formula (IVg), and formula (IVh), and where at least one Y is formula (IVa), formula (IVb), formula (IVc), formula (IVd), formula (IVe), formula (IVf), formula (IVg), and formula (IVh);

R' is selected from the group consisting of hydrogen, alkyl, reporter ligands, heteroatom substituted acyl, carboxylates, esters, alcohols, alkoxy, hydroxy alkyl, heteroatom substituted alkyl, carbamides, aldehydes, amines, amides, sulfur oxides, nitrogen oxides, and halides; and Z is selected from the group consisting of CO$_2$H, NH$_2$, and SH.

In particular embodiments, the present invention provides an oxocarbonamide peptide nucleic acid having the formula (IIa):

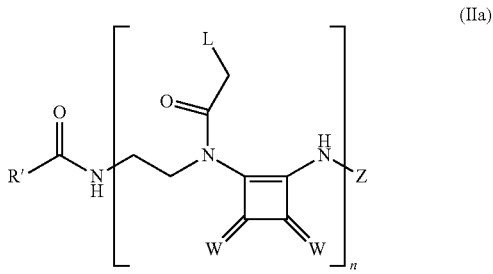

wherein W is O or S;

each L is independently selected from the group consisting of heteroatom substituted aryl, naturally occurring nucleobases, non-naturally occurring nucleobases, nucleobase binding groups, hydrogen, hydroxy, (C$_1$-C$_4$)alkanoyl, aromatic moieties, and reporter ligands, wherein at least one of L$^1$-L$^n$ is a heteroatom substituted aryl, naturally occurring nucleobase, non-naturally occurring nucleobase, nucleobase binding group, or DNA intercalator;

R' is selected from the group consisting of hydrogen, alkyl, amino protecting groups, reporter ligands, heteroatom substituted acyl, carboxylates, esters, alcohols, alkoxy, hydroxy alkyl, heteroatom substituted alkyl, carbamides, aldehydes, amines, heteroatom substituted amide, sulfur oxides, nitrogen oxides, halides, reporter ligands, intercalators, chelators, peptides, proteins, carbohydrates, lipids, steroids, oligonucleotides, and soluble and non-soluble polymers;

Z is selected from the group consisting of CO$_2$H, CONR'R''', SO$_3$H, NH$_2$, SH, SO$_2$NR'R'', NHR''R''', or NR'''COR'''', where R', R'', R''', and R'''' are independently selected from the group consisting of hydrogen, alkyl, amino protecting groups, reporter ligands, heteroatom substituted acyl, carboxylates, esters, alcohols, alkoxy, hydroxy alkyl, heteroatom substituted alkyl, carbamides, aldehydes, amines, amides, sulfur oxides, nitrogen oxides, halides, reporter ligands, intercalators, chelators, peptides, proteins, carbohydrates, lipids, steroids, oligonucleotides, and soluble and non-soluble polymers; and n is an integer from 1 to 100.

In certain embodiments, the present invention provides an oxocarbonamide peptide nucleic acid having the formula (III):

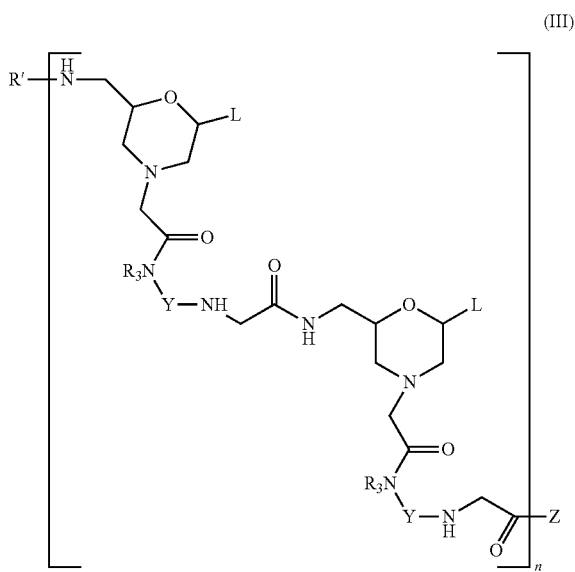

wherein:

each L is independently selected from the group consisting of heteroatom substituted aryl, naturally occurring nucleobases, non-naturally occurring nucleobases, nucleobase binding groups, hydrogen, hydroxy, (C$_1$-C$_4$)alkanoyl, aromatic moieties, and reporter ligands, wherein at least one of L$^1$-L$^n$ is a heteroatom substituted aryl, naturally occurring nucleobase, non-naturally occurring nucleobase, nucleobase binding group, or DNA intercalator;

each Y is independently selected from the group consisting of CH$_2$CO, formula (IVa), formula (IVb), formula (IVc), formula (IVd), formula (IVe), formula (IVf), formula (IVg), and formula (IVh), and where at least one Y is formula (IVa), formula (IVb), formula (IVc), formula (IVd), formula (IVe), formula (IVf), formula (IVg), and formula (IVh);

R' is selected from the group consisting of hydrogen, alkyl, amino protecting groups, reporter ligands, heteroatom substituted acyl, carboxylates, esters, alcohols, alkoxy, hydroxy alkyl, heteroatom substituted alkyl, carbamides, aldehydes, amines, amides, sulfur oxides, nitrogen oxides, halides, reporter ligands, intercalators, chelators, peptides, proteins, carbohydrates, lipids, steroids, oligonucleotides, and soluble and non-soluble polymers;

R$_3$ is selected from the group consisting of H, CH$_3$, and cationic polymers;

Z is selected from the group consisting of CO$_2$H, CONR'R''', SO$_3$H, NH$_2$, SH, SO$_2$NR'R'', NHR''R''', or NR'''COR'''', where R', R'', R''', and R'''' are independently selected from the group consisting of hydrogen, alkyl, amino protecting groups, reporter ligands, intercalators, chelators, peptides, proteins, carbohydrates, lipids, steroids, oligonucleotides, and soluble and non-soluble polymers; and n is an integer from 1 to 100. In certain aspects of the invention, the cationic polymer is a branched amine such as, for example, a polyamidoamine (PMAM) dendrimer or a polyethyleneimine (PEI). In some aspects of the invention, the cationic polymer is a polyammonium group (e.g., (CH$_2$)$_n$NR$_3$). Due to their structure and charge, cationic polymers are useful nucleic acid transfection agents and drug carriers.

In certain embodiments, the present invention provides an oxocarbonamide peptide nucleic acid having the formula (III):

wherein:

n is an integer from 1 to 100;

each L is independently selected from the group consisting of naturally occurring nucleobases, non-naturally occurring nucleobases, nucleobase binding groups, and DNA intercalators;

each Y is independently selected from the group consisting of CH$_2$CO, formula (IVa), formula (IVb), formula (IVc), formula (IVd), formula (We), formula (IVf), formula (IVg), and formula (IVh), and where at least one Y is formula (IVa), formula (IVb), formula (IVc), formula (IVd), formula (IVe), formula (IVf), formula (IVg), and formula (IVh);

R' is selected from the group consisting of hydrogen, alkyl, reporter ligands, heteroatom substituted acyl, carboxylates, esters, alcohols, alkoxy, hydroxy alkyl, heteroatom substituted alkyl, heteroatom substituted acyls, carbamides, aldehydes, amines, sulfur oxides, nitrogen oxides, and halides;

R$_3$ is selected from the group consisting of H, CH$_3$, and cationic polymers; and Z is selected from the group consisting of CO$_2$H, NH$_2$, and SH.

In particular embodiments, the present invention provides an oxocarbonamide peptide nucleic acid having the formula (IIIa):

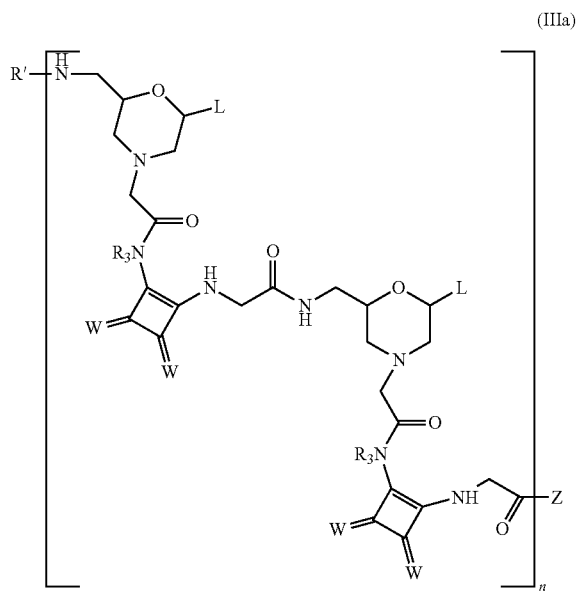

wherein W is O or S;

each L is independently selected from the group consisting of heteroatom substituted aryl, naturally occurring nucleobases, non-naturally occurring nucleobases, nucleobase binding groups, hydrogen, hydroxy, $(C_1-C_4)$alkanoyl, aromatic moieties, and reporter ligands, wherein at least one of $L^1-L^n$ is a naturally occurring nucleobase, non-naturally occurring nucleobase, nucleobase binding group, or DNA intercalator;

R' is selected from the group consisting of hydrogen, alkyl, amino protecting groups, reporter ligands, heteroatom substituted acyl, carboxylates, esters, alcohols, alkoxy, hydroxy alkyl, heteroatom substituted alkyl, carbamides, aldehydes, amines, sulfur oxides, nitrogen oxides, halides, reporter ligands, intercalators, chelators, peptides, proteins, carbohydrates, lipids, steroids, oligonucleotides, and soluble and non-soluble polymers;

$R_3$ is selected from the group consisting of H, $CH_3$, and cationic polymers;

Z is selected from the group consisting of $CO_2H$, CONR'R'', $SO_3H$, $NH_2$, SH, $SO_2NR'R''$, NHR'''R''', or NR'''COR'''', where R', R'', R''', and R'''' are independently selected from the group consisting of hydrogen, alkyl, amino protecting groups, reporter ligands, heteroatom substituted acyl, carboxylates, esters, alcohols, alkoxy, hydroxy alkyl, heteroatom substituted alkyl, carbamides, aldehydes, amines, amides, sulfur oxides, nitrogen oxides, halides, reporter ligands, intercalators, chelators, peptides, proteins, carbohydrates, lipids, steroids, oligonucleotides, and soluble and non-soluble polymers; and n is an integer from 1 to 100.

In certain aspects of the invention, n may be an integer from 8 to 60, 10 to 50, 15 to 30, or 18 to 25. In some embodiments, n is 8, 9, 10, 11, 12, 13, 14, 15, 16, 17, 18, 19, 20, 21, 22, 23, 24, 25, 26, 27, 28, 29, or 30, or any range derivable therein.

In certain aspects of the invention, no Y is $CH_2CO$. In some aspects of the invention all Ys are formula (IVa), formula (IVe), or a combination of formula (IVa) and formula (IVe).

The oligonucleotide analogs of the present invention may be employed in a wide range of applications, particularly in applications involving hybridization. In one embodiment, the present invention provides a method for detecting a target nucleic acid molecule, comprising: (a) providing an oxocarbonamide peptide nucleic acid comprising a sequence complementary to a sequence of a target nucleic acid molecule; (b) contacting the oxocarbonamide peptide nucleic acid with the target nucleic molecule under conditions that allow the oxocarbonamide peptide nucleic acid to hybridize with the target molecule; and (c) detecting the hybridization. The target nucleic acid molecule may be, for example, a DNA or an RNA molecule. The RNA molecule may be, for example, an mRNA, rRNA, tRNA, miRNA, or siRNA.

To facilitate the detection of a target molecule, one or both of the oxocarbonamide peptide nucleic acid probe or the target molecule may be labeled. A number of different labels may be used in the present invention such as fluorophores, chromophores, radiophores, enzymatic tags, antibodies, chemiluminescence, electroluminescence, metal nanoparticles, quantum dots, magnetic particles, and affinity labels. One of skill in the art will recognize that these and other labels not mentioned herein can be used with success in this invention.

Examples of affinity labels include, but are not limited to the following: an antibody, an antibody fragment, a receptor protein, a hormone, biotin, DNP, a molecular imprint, or any polypeptide/protein molecule that binds to an affinity label.

Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, but are not limited to the following: all of the Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDyes™, including but not limited to $Cy_2$™, $Cy_3$™, and $Cy_5$™, DNA intercalating dyes, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, and Texas Red®.

In certain aspects of the invention, the oxocarbonamide peptide nucleic acid probe or the target molecule is immobilized on a solid support. Non-limiting examples of solid supports include: nitrocellulose, nylon membrane, glass, activated quartz, activated glass, polyvinylidene difluoride (PVDF) membrane, polystyrene substrates, polyacrylamide-based substrate, other polymers, copolymers, or crosslinked polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules). A solid support may be in the form of, for example, a bead, a column, or a chip.

In one embodiment, the present invention provides an array comprising a plurality of oxocarbonamide peptide nucleic acid probes immobilized on a solid support. In particular embodiments, the solid support is a chip or a bead. In certain aspects of the invention, the array comprises at least 10, 20, 30, 40, 50, 60, 70, 80, 90, 100, 150, 200, 300, 400, 500, 600, 700, 800, 900, 1000, 10000, 20000, 30000, 40000, 50000, 60000, 70000, 80000, 90000, or 100000, or any range derivable therein, different oxocarbonamide peptide oligonucleotide probes.

In certain embodiments, the present invention provides a method for detecting one or more target nucleic acid molecules in a multiplexed assay, comprising: (a) providing a plurality of different oxocarbonamide peptide nucleic acids, wherein each different oxocarbonamide peptide nucleic acid is covalently attached to a defined location on an array; (b) contacting a sample comprising the one or more target nucleic acid molecules with the array under conditions that allow the one or more target nucleic acid molecules to hybridize to complementary oxocarbonamide peptide nucleic acids on the array; and (c) detecting the hybridization. In particular embodiments, the plurality of nucleic acid molecules is a plurality of miRNA molecules. In certain embodiments, the array comprises a plurality of fluorescently encoded microspheres ("beads").

In another aspect, the invention provides a method for amplifying a target nucleic acid molecule. The method involves (a) incubating a first oxocarbonamide peptide nucleic acid of the invention with a target molecule under conditions that allow the first oxocarbonamide peptide nucleic acid to bind the target molecule; and (b) extending the first nucleic acid with the target molecule as a template. The method may further comprise contacting the target molecule with a second oxocarbonamide peptide nucleic acid that binds to a different region of the target molecule than the first oxocarbonamide peptide nucleic acid. In various embodiments, the sequence of the target molecule is known or unknown.

In certain aspects, the association constant ($K_a$) of the oxocarbonamide peptide nucleic acid toward a complementary target molecule is higher than the association constant of the complementary strands of the double stranded target molecule. In some embodiments, the melting temperature of a duplex between the oxocarbonamide peptide nucleic acid and a complementary target molecule is higher than the melting temperature of the complementary strands of the double stranded target molecule.

In one aspect, the present invention provides pharmaceutical composition comprising an oxocarbonamide peptide nucleic acid for treatment of a disease curable by an antisense technology. In one embodiment, the invention provides a method for inhibiting the expression of a target nucleic acid in a cell. The method comprises introducing into the cell a oxocarbonamide peptide nucleic acid of the invention in an amount sufficient to specifically attenuate expression of the target nucleic acid. The introduced oxocarbonamide peptide nucleic acid has a nucleotide sequence that is complementary to a region of the target nucleic acid sequence. In another aspect, the invention provides a method for preventing, stabilizing, or treating a disease, disorder, or condition associated with a target nucleic acid in a mammal. This method comprises introducing into the mammal oxocarbonamide peptide nucleic acid of the invention in an amount sufficient to specifically attenuate expression of the target nucleic acid, wherein the introduced oxocarbonamide peptide nucleic acid has a nucleotide sequence that is complementary to a region of the target nucleic acid. In particular embodiments, the oxocarbonamide peptide nucleic acid has a nucleotide sequence that is complementary to a region of between about 10 to about 100, about 10 to about 50, about 10 to about 30, about 15 to about 30, or about 17 to about 25, nucleotides of the target nucleic acid sequence. In some embodiments, the introduced oxocarbonamide peptide nucleic acid is single stranded or double stranded. Where the oxocarbonamide peptide nucleic acid is double stranded, both strands may be oxocarbonamide peptide nucleic acids or one strand may be an oxocarbonamide peptide nucleic acid and the other strand may be a DNA, RNA, or an oligonucleotide analog such as a PNA or LNA.

Exemplary mammals that can be treated using the methods of the invention include humans, primates, animals of veterinary interest (e.g., cows, sheep, goats, buffaloes, and horses), and domestic pets (e.g., dogs and cats). Exemplary cells in which one or more target genes can be silenced using the methods of the invention include invertebrate, plant, bacteria, yeast, and vertebrate (e.g., mammalian) cells.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A shows one scheme for the synthesis of peptide nucleic acid monomers according to the method of Howarth et al. (1997). FIG. 6B shows examples of additional peptide nucleic acid monomers that may be prepared according to the scheme shown in FIG. 6A. FIG. 6C shows two examples of peptide nucleic acid monomers modified with squaric acid.

FIG. 7A shows a scheme for the synthesis of a β-aminoalainine monomer modified with a nucleobase according to the protocol of Fujii et al. (1998). FIG. 7B shows the β-aminoalainine nucleoside monomer modified with squaric acid.

DESCRIPTION OF ILLUSTRATIVE EMBODIMENTS

A. The Present Invention

The present invention provides novel oxocarbon acid incorporated peptide nucleic acids (OxoPNAs) that provide increased stability, sensitivity, and specificity as compared to their natural DNA and RNA counterparts. The OxoPNAs of the invention generally comprise nucleobases linked to an oxocarbon acid amide incorporated peptide backbone. The nucleobases may include any of the four main naturally occurring DNA bases (i.e., thymine, cytosine, adenine, or guanine) or other naturally occurring nucleobases (e.g., inosine, uracil, 5-methylcytosine, or thiouracil) or artificial bases (e.g., bromothymine, azaadenines, or azaguanines, etc.) attached to a peptide backbone through a suitable linker. The oxocarbon acid may be squaric acid, deltic acid, croconic acid, rhodizonic acid, or their corresponding thioxocarbon acids.

The present invention also provides a variety of methods employing the OxoPNAs of the present invention. As described herein, the oligonucleotide analogs of the present invention may be employed in a wide range of applications, particularly in applications involving hybridization. For example, the present invention provides methods for the detection and functional analysis of nucleic acid molecules, including miRNAs and other non-coding RNAs. In addition, the present invention also provides methods for antisense-based intervention targeted against disease-associated nucleic acid molecules.

B. Oxocarbon Acid Amide Modified PNAs

Figure 1:
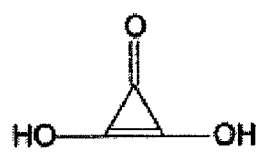
FIG. 1 shows the oxocarbon acids: deltic acid, thio-deltic acid, squaric acid, thio-squaric acid, croconic acid, thio-croconic acid, rhodizonic acid, and thio-rhodizonic acid.
Figure 1:
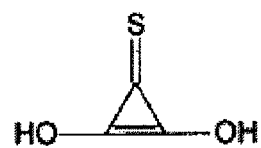
Figure 1:
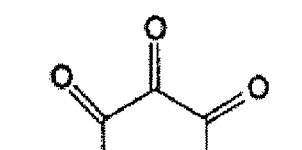
Figure 1:
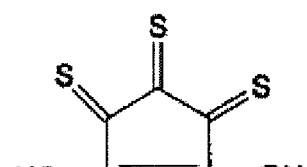
Figure 1:
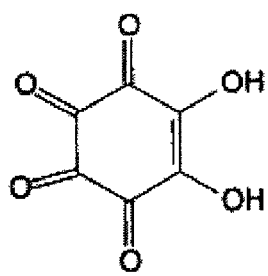
Figure 1:
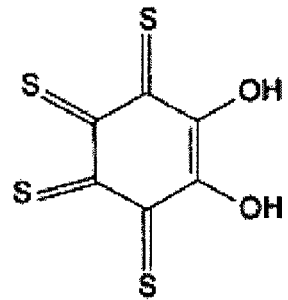
Figure 1:
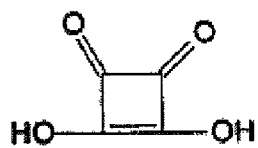
Figure 1:
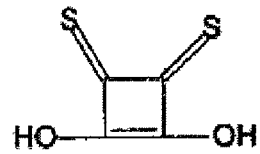

The present invention provides novel oxocarbon acid amide (i.e., "oxocarbonamide") incorporated peptide oligonucleotides. Oxocarbon acids are a class of organic compounds that are vinylogs of carboxylic acids, that is the OH and CO groups are joined through a vinylic unsaturation forming a cyclic non-aromatic ring. Furthermore, the carbon atoms not involved in the acidic moiety are substituted by oxygen and are present as carbonyl or hydroxy functions. Cyclic oxocarbon compounds have the general formula $C_xO_x$, wherein $x \geq 3$. Examples of oxocarbon acids are deltic acid, squaric acid, croconic acid, and rhodizonic acid (FIG. 1).

Squaric acid derivatives have been shown to function as amino acid-like analogs. For example, Porter et al. demonstrated that a squaric acid derivative of the thioproline CT5219, a small molecule VLA-4 antagonist, was also a potent VLA-4 antagonist and had an improved pharmokinetic profile compared to CT5219 (Porter et al., 2002).

The squaryl group has been evaluated as a mimic of the phosphate group in modified oligodeoxynucleotides (Sato et al., 2002). Squaric acid is a dibasic acid with two acidic hydroxyl groups and two carbonyl groups. Nucleophilic substitution of the squaric acid esters with amines gives the corresponding diamides. Sato et al. reported the synthesis of oligonucleotide analogues containing a single squaryldiamide internucleotide linkage between two thymidines (TsqT). The structure of the TsqT as reported by Sato et al. is as follows:

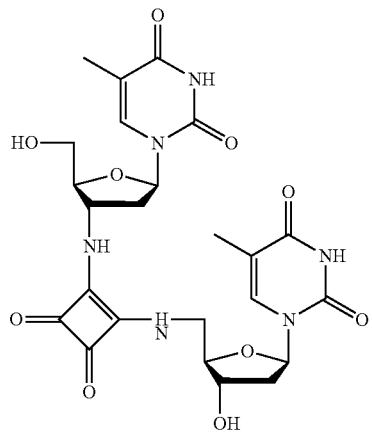

The present invention employs squaryldiamides, and other oxocarbonamides, in the design of modified peptide nucleic acids. In one embodiment, a squaryldiamide modified peptide nucleic acid of the present invention has the structure:

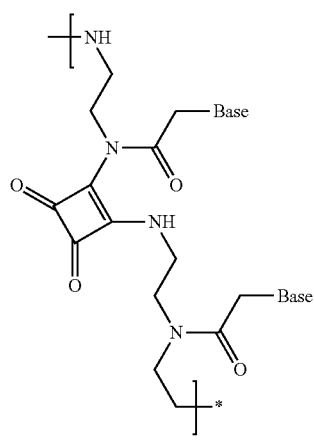

A "peptide nucleic acid," also known as a "PNA," "peptide-based nucleic acid analog," or "PENAM," generally has enhanced sequence specificity, binding properties, and resistance to enzymatic degradation in comparison to molecules such as DNA and RNA (Egholm et al., 1993; PCT/EP/01219). A PNA typically comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety. Various PNAs have been described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference.

Other nucleotide analogs include, for example, a locked nucleic acid or "LNA." An LNA monomer is a bi-cyclic compound that is structurally similar to RNA nucleosides. LNAs have a furanose conformation that is restricted by a methylene linker that connects the 2'-O position to the 4'-C position, as described in Koshkin et al., 1998a and 1998b and Wahlestedt et al., 2000.

Typical structures of a deoxyribonucleic acid (DNA), locked nucleic acid (LNA), and a peptide nucleic acid (PNA) are:

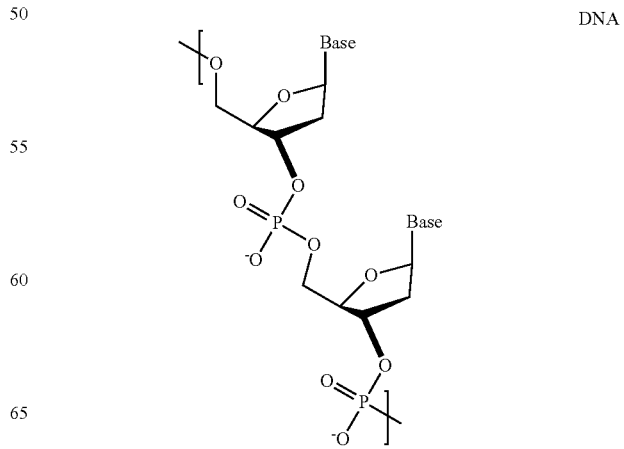

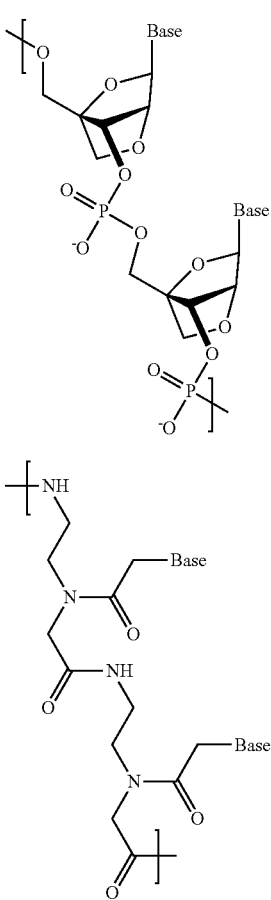

The preparation of PNA oligomers may be based on standard solid phase peptide synthesis protocols such as those disclosed in WO 92/20702; U.S. Pat. No. 5,539,082; and Mc Cairn et al. (2006).

Figure 2:
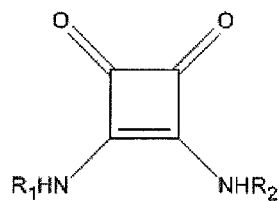
FIG. 2 shows abasic monomers of squaric acid amides and reactive derivatives of squaric acid.
Figure 2:
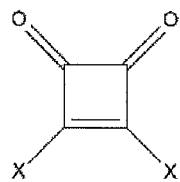
Figure 2:
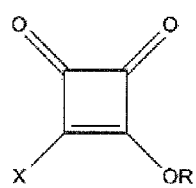
Figure 2:
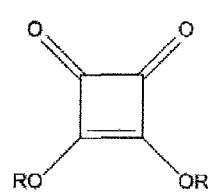
Figure 2:
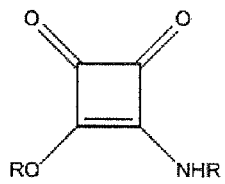
Figure 2:
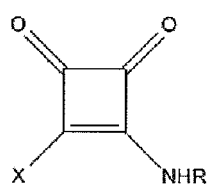
Figure 2:
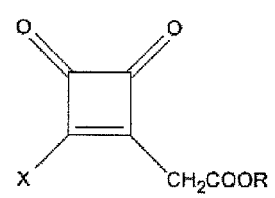
Figure 3:
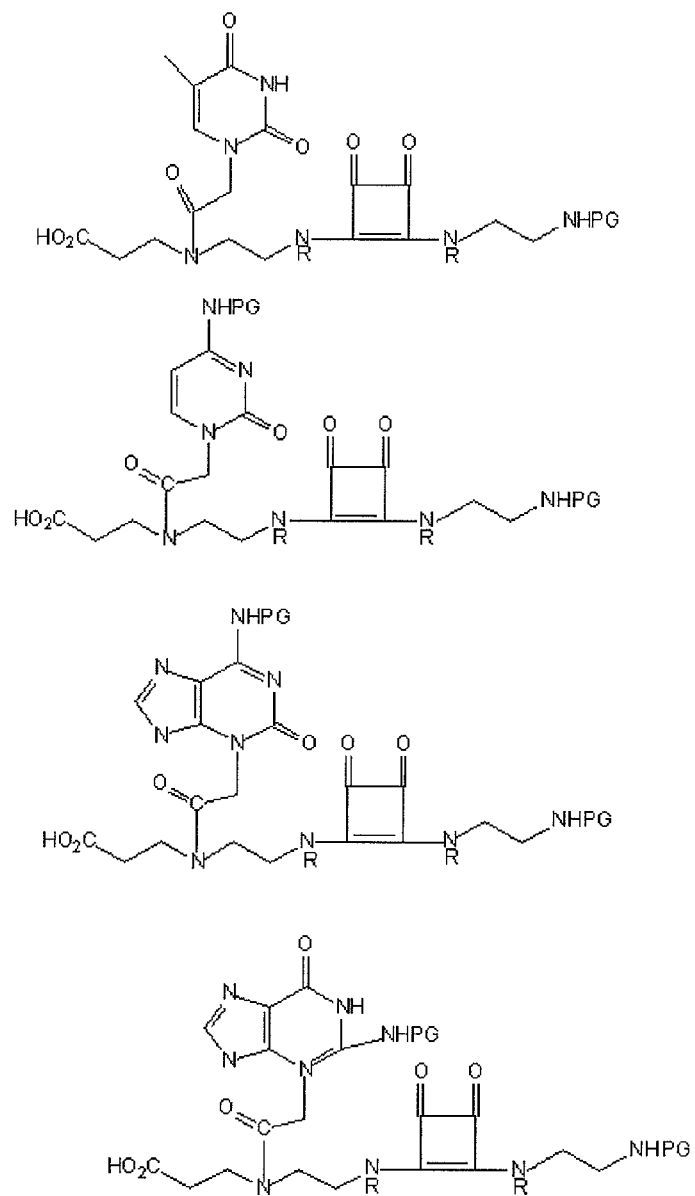
FIG. 3 shows squaric acid amide peptide nucleic acid (SquarPNA) monomers.
Figure 4:
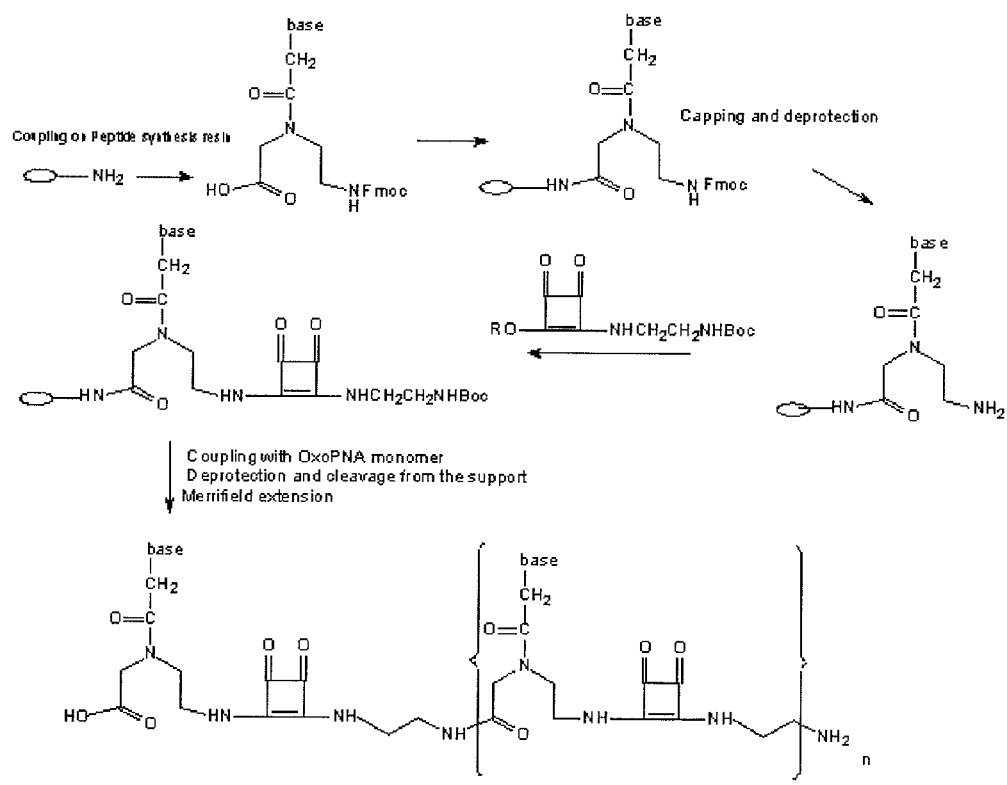
FIG. 4 shows one scheme for the solid phase synthesis of OxoPNAs.
Figure 5:
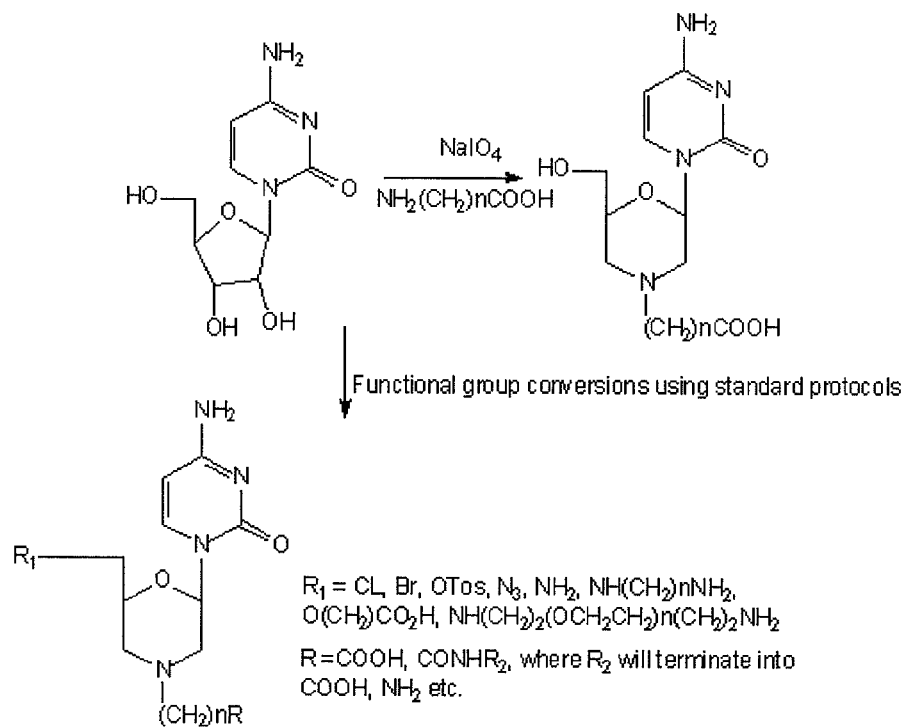
FIG. 5 shows one scheme for the synthesis of morpholino nucleosides for incorporation in OxoPNAs. Morpholino nucleotide synthesis may be performed according to the method of Girault et al. (1996) (incorporated by reference).
Figure 6A:
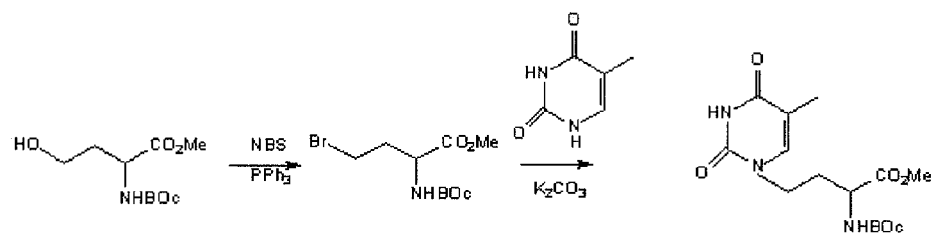
FIGS. 6A, 6B, and 6C.
Figure 6B:
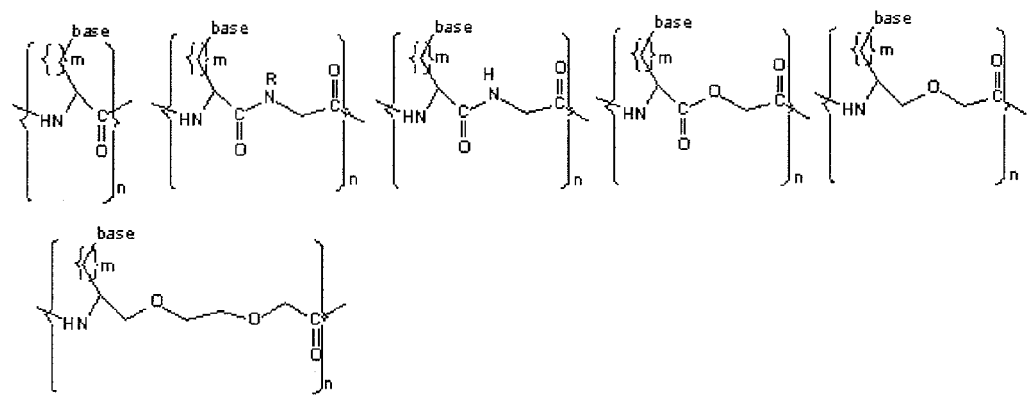
Figure 6C:
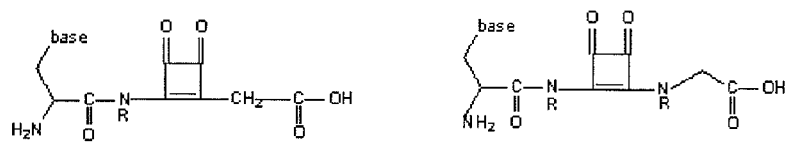
Figure 7A:
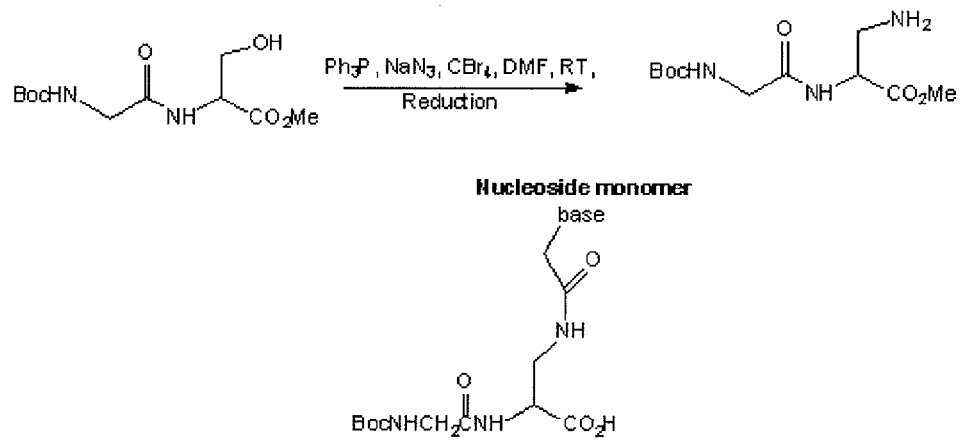
FIGS. 7A and 7B.
Figure 7B:
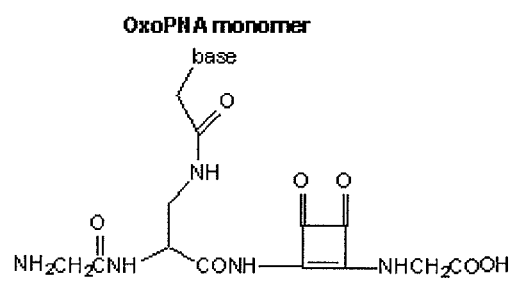
Figure 8:
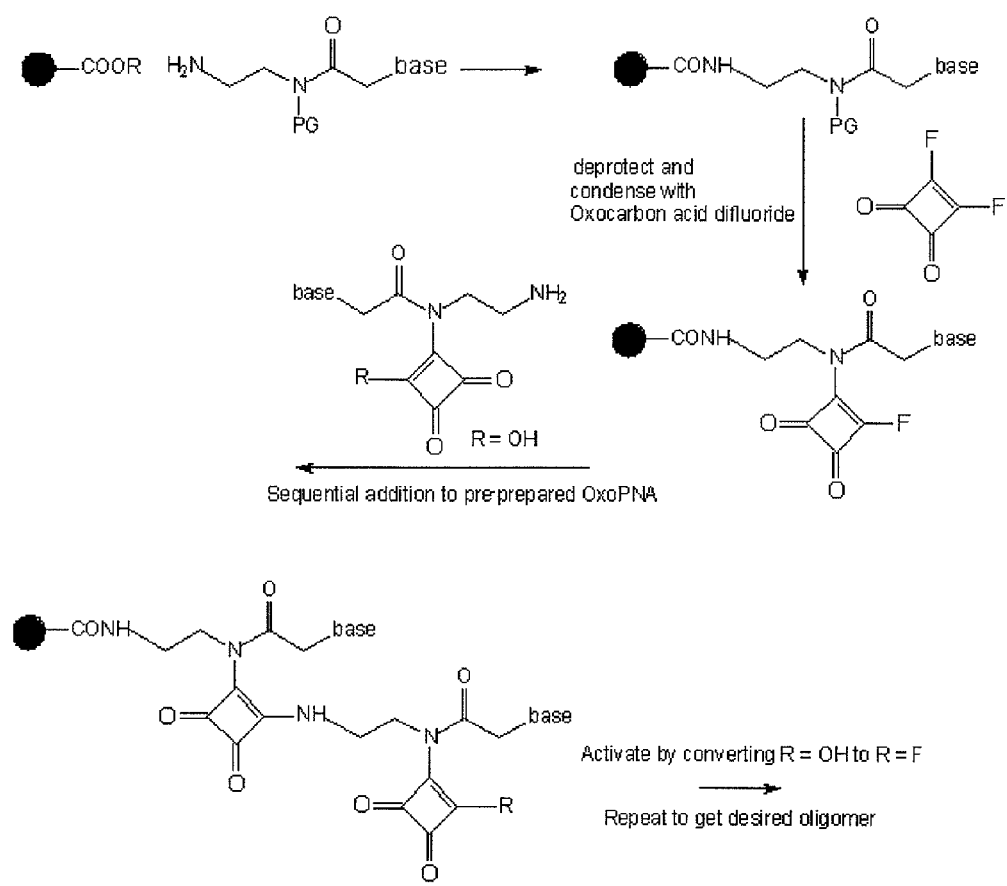
FIG. 8 shows one scheme for the solid phase synthesis of OxoPNAs using reactive derivatives of squaric acid. Although difluoro squaric acid is used in this example, other reactive halogen derivatives, such as dichloro squaric acid, could be used. Dilkyl ester derivatives of squaric acid could also be used.
Figure 9:
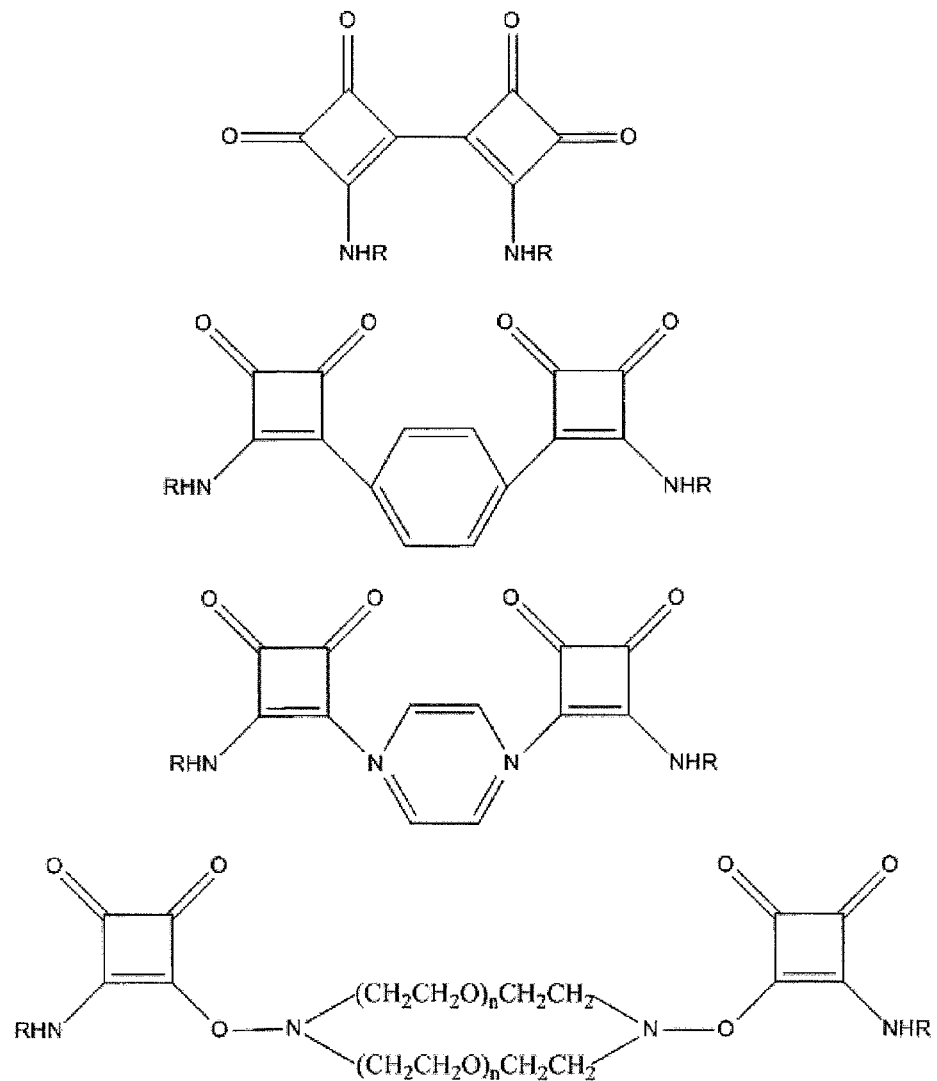
FIG. 9 shows abasic dimers of squaric acid amides.

Solid phase synthesis is also a convenient strategy for making the OxoPNAs of the present invention. Examples of reactive derivatives of squaric acid and OxoPNA monomers, which may be used in the synthesis of OxoPNAs are illustrated in FIGS. 1 and 2, respectively. Examples of synthesis schemes for OxoPNAs are provided in FIGS. 4 to 8. Although the exemplary synthesis schemes in FIGS. 4 to 8 show squaric acid amides, it will be understood by those in the art that other oxocarbon acid amides could also be used to synthesize OxoPNAs. The synthesis of OxoPNAs may be performed on commercially available synthesizers using commercially available reagents. In certain embodiments, resins such as 5-(4-Fmoc-aminomethyl-3,5-dimethoxyphenoxy)valeric acid (PAL) or 5-(9-Fmoc-aminoxanthen-2-oxy)valeric acid (XAL) may be employed. The resins may be immobilized with functional groups such as $NH_2$ and COOH. The amino or carboxy end of the OxoPNA may be attached to the resin by establishing an amide bond. In addition, commercially available microsphere (e.g., Luminex beads) are functionalized with, for example, COOH and can be modified to make an amide bond for attachment of OxoPNAs.

The oxocarbonamide peptide nucleic acids of the present invention have improved stability, sensitivity, and specificity for their target sequences, which make them well suited to a variety of applications including, for example, the detection, analysis, and capture of miRNAs, and other small nucleic acids; and as antisense molecules for the selective gene knock-down.

C. Chemical Group Definitions

As used herein, the term "amino" means $-NH_2$; the term "nitro" means $-NO_2$; the term "halo" designates $-F$, $-Cl$, $-Br$ or $-I$; the term "mercapto" means $-SH$; the term "cyano" means $-CN$; the term "azido" means $-N_3$; the term "silyl" means $-SiH_3$, and the term "hydroxy" means $-OH$.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted alkyl$_{(Cn)}$, and heteroatom-substituted alkyl$_{(Cn)}$. The term "heteroatom-unsubstituted alkyl$_{(Cn)}$" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted alkyl$_{(C1-C10)}$ has 1 to 10 carbon atoms. The groups, $-CH_3$ (Me), $-CH_2CH_3$ (Et), $-CH_2CH_2CH_3$ (n-Pr), $-CH(CH_3)_2$ (iso-Pr), $-CH(CH_2)_2$ (cyclopropyl), $-CH_2CH_2CH_2CH_3$ (n-Bu), $-CH(CH_3)CH_2CH_3$ (sec-butyl), $-CH_2CH(CH_3)_2$ (iso-butyl), $-C(CH_3)_3$ (tert-butyl), $-CH_2C(CH_3)_3$ (neopentyl), cyclobutyl, cyclopentyl, and cyclohexyl, are all non-limiting examples of heteroatom-unsubstituted alkyl groups. The term "heteroatom-substituted alkyl$_{(Cn)}$" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted alkyl$_{(C1-C10)}$ has 1 to 10 carbon atoms. The following groups are all non-limiting examples of heteroatom-substituted alkyl groups: trifluoromethyl, $-CH_2F$, $-CH_2Cl$, $-CH_2Br$, $-CH_2OH$, $-CH_2OCH_3$, $-CH_2OCH_2CF_3$, $-CH_2OC(O)CH_3$, $-CH_2NH_2$, $-CH_2NHCH_3$, $-CH_2N(CH_3)_2$, $-CH_2CH_2Cl$, $-CH_2CH_2OH$, $CH_2CH_2OC(O)CH_3$, $-CH_2CH_2NHCO_2C(CH_3)_3$, and $-CH_2Si(CH_3)_3$.

The term "aryl" includes heteroatom-unsubstituted aryl, heteroatom-substituted aryl, heteroatom-unsubstituted aryl$_{(Cn)}$, heteroatom-substituted aryl$_{(Cn)}$, heteroaryl, heterocyclic aryl groups, carbocyclic aryl groups, biaryl groups, and single-valent radicals derived from polycyclic fused hydrocarbons (PAHs). The term "heteroatom-unsubstituted aryl$_{(Cn)}$" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted aryl$_{(C6-C10)}$ has 6 to 10 carbon atoms. Non-limiting examples of heteroatom-unsubstituted aryl groups include phenyl (Ph), methylphenyl, (dimethyl)phenyl, $-C_6H_4CH_2CH_3$, $-C_6H_4CH_2CH_2CH_3$, $-C_6H_4CH(CH_3)_2$, $-C_6H_4CH(CH_2)_2$, $-C_6H_3(CH_3)CH_2CH_3$, $C_6H_4CH=CH_2$, $-C_6H_4CH=CHCH_3$, $-C_6H_4C\equiv CH$, $-C_6H_4C\equiv CCH_3$, naphthyl, and the radical derived from biphenyl. The term "heteroatom-substituted aryl$_{(Cn)}$" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted heteroaryl$_{(C1-C10)}$ has 1 to 10 carbon atoms. Non-limiting examples of heteroatom-substituted aryl groups include the groups: —$C_6H_4F$, —$C_6H_4Cl$, —$C_6H_4Br$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$—$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, $C_6H_4CONH_2$, $C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl.

The term "aralkyl" includes heteroatom-unsubstituted aralkyl, heteroatom-substituted aralkyl, heteroatom-unsubstituted aralkyl$_{(Cn)}$, heteroatom-substituted aralkyl$_{(Cn)}$, heteroaralkyl, and heterocyclic aralkyl groups. The term "heteroatom-unsubstituted aralkyl$_{(Cn)}$" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted aralkyl$_{(C7-C10)}$ has 7 to 10 carbon atoms. Non-limiting examples of heteroatom-unsubstituted aralkyls are: phenylmethyl (benzyl, Bn) and phenylethyl. The term "heteroatom-substituted aralkyl$_{(Cn)}$" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted heteroaralkyl$_{(C2-C10)}$ has 2 to 10 carbon atoms.

The term "acyl" includes straight-chain acyl, branched-chain acyl, cycloakyl, cyclic acyl, heteroatom-unsubstituted acyl, heteroatom-substituted acyl, heteroatom-unsubstituted acyl$_{(Cn)}$, heteroatom-substituted acyl$_{(Cn)}$, alkylcarbonyl, alkoxycarbonyl and aminocarbonyl groups. The term "heteroatom-unsubstituted acyl$_{(Cn)}$" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted acyl$_{(C1-C10)}$ has 1 to 10 carbon atoms. The groups, —CHO, —C(O)CH$_3$, —C(O)CH$_2$CH$_3$, —C(O)CH$_2$CH$_2$CH$_3$, C(O)CH(CH$_3$)$_2$, —C(O)CH(CH$_2$)$_2$, —C(O)C$_6$H$_5$, C(O)C$_6$H$_4$—CH$_3$, —C(O)C$_6$H$_4$CH$_2$CH$_3$, and —COC$_6$H$_3$(CH$_3$)$_2$, are non-limiting examples of heteroatom-unsubstituted acyl groups. The term "heteroatom-substituted acyl$_{(Cn)}$" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted acyl$_{(C1-C10)}$ has 1 to 10 carbon atoms. The groups, —C(O)CH$_2$CF$_3$, —CO$_2$H, —CO$_2$CH$_3$, —CO$_2$CH$_2$CH$_3$, CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted alkoxy$_{(Cn)}$, and heteroatom-substituted alkoxy$_{(Cn)}$. The term "heteroatom-unsubstituted alkoxy$_{(Cn)}$" refers to a group, having the structure —OR, in which R is a heteroatom-unsubstituted alkyl$_{(Cn)}$, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted alkoxy$_{(Cn)}$" refers to a group, having the structure —OR, in which R is a heteroatom-substituted alkyl$_{(Cn)}$, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted alkenyloxy$_{(Cn)}$, and heteroatom-substituted alkenyloxy$_{(Cn)}$. The term "heteroatom-unsubstituted alkenyloxy$_{(Cn)}$" refers to a group, having the structure —OR, in which R is a heteroatom-unsubstituted alkenyl$_{(Cn)}$, as that term is defined above. The term "heteroatom-substituted alkenyloxy$_{(Cn)}$" refers to a group, having the structure —OR, in which R is a heteroatom-substituted alkenyl$_{(Cn)}$, as that term is defined above.

The term "alkynyloxy" includes straight-chain alkynyloxy, branched-chain alkynyloxy, cycloalkenyloxy, cyclic alkynyloxy, heteroatom-unsubstituted alkynyloxy, heteroatom-substituted alkynyloxy, heteroatom-unsubstituted alkynyloxy$_{(Cn)}$, and heteroatom-substituted alkynyloxy$_{(Cn)}$. The term "heteroatom-unsubstituted alkynyloxy$_{(Cn)}$" refers to a group, having the structure —OR, in which R is a heteroatom-unsubstituted alkynyl$_{(Cn)}$, as that term is defined above. The term "heteroatom-substituted alkynyloxy$_{(Cn)}$" refers to a group, having the structure —OR, in which R is a heteroatom-substituted alkynyl$_{(Cn)}$, as that term is defined above.

The term "aryloxy" includes heteroatom-unsubstituted aryloxy, heteroatom-substituted aryloxy, heteroatom-unsubstituted aryloxy$_{(Cn)}$, heteroatom-substituted aryloxy$_{(Cn)}$, heteroaryloxy, and heterocyclic aryloxy groups. The term "heteroatom-unsubstituted aryloxy$_{(Cn)}$" refers to a group, having the structure —OAr, in which Ar is a heteroatom-unsubstituted aryl$_{(Cn)}$, as that term is defined above. A non-limiting example of a heteroatom-unsubstituted aryloxy group is —OC$_6$H$_5$. The term "heteroatom-substituted aryloxy$_{(Cn)}$" refers to a group, having the structure —OAr, in which Ar is a heteroatom-substituted aryl$_{(Cn)}$, as that term is defined above.

The term "aralkyloxy" includes heteroatom-unsubstituted aralkyloxy, heteroatom-substituted aralkyloxy, heteroatom-unsubstituted aralkyloxy$_{(Cn)}$, heteroatom-substituted aralkyloxy$_{(Cn)}$, heteroaralkyloxy, and heterocyclic aralkyloxy groups. The term "heteroatom-unsubstituted aralkyloxy$_{(Cn)}$" refers to a group, having the structure —OAr, in which Ar is a heteroatom-unsubstituted aralkyl$_{(Cn)}$, as that term is defined above. The term "heteroatom-substituted aralkyloxy$_{(Cn)}$" refers to a group, having the structure —OAr, in which Ar is a heteroatom-substituted aralkyl$_{(Cn)}$, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted acyloxy$_{(Cn)}$, heteroatom-substituted acyloxy$_{(Cn)}$, alkylcarbonyloxy, arylcarbonyloxy, alkoxycarbonyloxy, aryloxycarbonyloxy, and carboxylate groups. The term "heteroatom-unsubstituted acyloxy$_{(Cn)}$" refers to a group, having the structure —OAc, in which Ac is a heteroatom-unsubstituted acyl$_{(C_n)}$, as that term is defined above. For example, —OC(O)CH$_3$ is a non-limiting example of a heteroatom-unsubstituted acyloxy group. The term "heteroatom-substituted acyloxy$_{(C_n)}$" refers to a group, having the structure —OAc, in which Ac is a heteroatom-substituted acyl$_{(C_n)}$, as that term is defined above. For example, —OC(O)OCH$_3$ and —OC(O)NHCH$_3$ are non-limiting examples of heteroatom-unsubstituted acyloxy groups.

A DNA intercalating agent is a ligand of an appropriate size and chemical nature to fit in between base pairs of DNA. These ligands are mostly polycyclic, aromatic, and planar. Non-limiting examples of DNA intercalators include ethidium bromide, proflavine, daunomycin, doxorubicin, and thalidomide.

D. Nucleic Acid Detection

The stability, sensitivity, and specificity of the oxocarbonamide peptide nucleic acids of the present invention, make them a useful tool in diagnostics and molecular biology. While the compounds of the present invention are useful in the detection and analysis of any nucleic acids, it is contemplated that they will be particularly useful in the detection of small RNA molecules such as miRNA molecules, which often require the use of sensitive analysis tools due to their size and low level of expression.

In certain embodiments, the oxocarbonamide peptide nucleic acids of the present invention may be used as hybridization probes for the detection of complementary nucleic acid sequences. Sequence-specific nucleic acid hybridization assays (e.g., Northern blotting, Southern blotting, and microarray analysis) are commonly used for the detection of specific genetic sequences as indicators of genetic anomalies, mutations, and disease propensity. In addition, they are used for the detection of various biological agents and infectious pathogens.

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridizes" or "capable of hybridizing" encompasses the terms "stringent conditions" or "high stringency" and the terms "low stringency" or "low stringency conditions." As used herein "stringent conditions" or "high stringency" are those conditions that allow hybridization between or within one or more nucleic acid strands containing complementary sequences, but preclude hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA, miRNA, or siRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acids, the length and nucleobase content of the target sequences, the charge composition of the nucleic acids, the presence of nucleic acid analogues in the nucleic acid molecules, and to the presence or concentration of formamide, tetramethylammonium chloride or other solvents in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

The present invention may be employed in solution hybridization as well as in solid phase hybridization. The hybridization conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,486 and 5,851,772.

To detect hybridization, it will be advantageous to employ an appropriate detection moiety. Recognition moieties incorporated into primers, incorporated into the amplified product during amplification, or attached to probes are useful in the identification of nucleic acid molecules. A number of different labels may be used for this purpose such as fluorophores, chromophores, radiophores, enzymatic tags, antibodies, chemiluminescence, electroluminescence, affinity labels, noble metal nanoparticles, quantum dots, magnetic particles, etc. One of skill in the art will recognize that these and other labels not mentioned herein can be used with success in this invention.

Examples of affinity labels include, but are not limited to the following: an antibody, an antibody fragment, a receptor protein, a hormone, biotin, DNP, or any polypeptide/protein molecule that binds to an affinity label.

Examples of enzyme tags include enzymes such as urease, alkaline phosphatase, or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, but are not limited to the following: all of the Alexa Fluor® dyes, AMCA, BODIPY® 630/650, BODIPY® 650/665, BODIPY®-FL, BODIPY®—R6G, BODIPY®-TMR, BODIPY®-TRX, Cascade Blue®, CyDyes™, including but not limited to Cy$_2$™, Cy$_3$™, and Cy$_5$™, DNA intercalating dyes, 6-FAM™, Fluorescein, HEX™, 6-JOE, Oregon Greene 488, Oregon Green® 500, Oregon Greene 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, and Texas Red®.

Detection can result in qualitative identification, semi-quantitative identification, or quantitative identification of the target molecule. Qualitative detection includes detection of the presence of the molecule, without any correlation to an amount of the molecule in the sample that was tested. Semi-quantitative detection permits not only detection of the target molecule, but correlation of the signal to a basal level of target molecule in the sample that was tested. For example, it may indicate a minimum threshold amount of the target molecule was present in the sample. Quantitative detection permits the practitioner to determine the amount of target molecule present in the original sample over a wide range of amounts. In general, quantitative detection compares the amount detected to a reference or standard that is either previously generated (e.g., a standard curve) or generated at the time of the assay for the target molecule using internal controls. Numerous techniques for performing quantitative and semi-quantitative analyses are known to those of skill in the art.

Arrays and gene chip technology provide a means of rapidly screening a large number of nucleic acid samples for their ability to hybridize to oxocarbonamide peptide nucleic acid molecules immobilized on a solid substrate. These techniques involve quantitative methods for analyzing large numbers of miRNA molecules, or other nucleic acid sequences, rapidly and accurately. Basically, an array or gene chip consists of a solid substrate upon which an array of single stranded oxocarbonamide peptide nucleic acid molecules have been attached. For screening, the chip or array is contacted with a single stranded DNA or RNA sample, which is allowed to hybridize under stringent conditions. The chip or array is then scanned to determine which probes have hybridized.

The ability to directly synthesize on or attach polynucleotide probes to solid substrates is well known in the art. See U.S. Pat. Nos. 5,837,832 and 5,837,860, both of which are expressly incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents (Running et al., 1990; Newton et al., 1993). When immobilized onto a substrate, the probes are stabilized and therefore may be used repeatedly. In general terms, hybridization is performed on an immobilized nucleic acid target or a probe molecule that is attached to a solid surface such as nitrocellulose, nylon membrane, or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules.

In certain embodiments, the present invention is used in conjunction with Luminex® xMAP® technology. The Luminex technology allows the quantitation of nucleic acid products immobilized on fluorescently encoded microspheres. By dyeing microspheres with 10 different intensities each of two spectrally distinct fluorochromes, 100 fluorescently distinct populations of microspheres are produced. By using three or more spectrally distinct fluorochromes at different intensity levels, even greater numbers of fluorescently distinct populations can be created. These individual populations (sets) can represent individual detection sequences and the magnitude of hybridization on each set can be detected individually. The magnitude of the hybridization reaction is measured using a third spectrally distinct fluorochrome called a reporter. The reporter molecule signals the extent of the reaction by attaching to the molecules on the microspheres. As both the microspheres and the reporter molecules are labeled, digital signal processing allows the translation of signals into real-time, quantitative data for each reaction. The Luminex technology is described, for example, in U.S. Pat. Nos. 5,736,330, 5,981,180, and 6,057,107, all of which are specifically incorporated by reference.

The present invention may also be used in conjunction with a competitive binding assay format. In general, this format involves a detection sequence coupled to a solid surface, and a labeled sequence complementary to the detection sequence in solution. With this format, the target sequence in the sample being assayed does not need to be labeled. Rather, the target sequence's presence in the sample is detected because it competes with the labeled complement for hybridization with the immobilized detection sequence. Thus, if the target sequence is present in the sample, the signal decreases as compared to a sample lacking the target sequence.

The Luminex xMAP technology described above can be used in a competitive binding assay format. In general, this format would comprise an oxocarbonamide peptide nucleic acid detection molecule immobilized on a labeled bead, a labeled sequence complementary to the detection sequence, exposing the immobilized detection sequence and the labeled complement to a nucleic acid sample under hybridizing conditions, and detecting the presence or absence of the target sequence in the sample. The use of the Luminex technology in a competitive binding assay format is described in U.S. Pat. Nos. 5,736,330 and 6,057,107, incorporated herein by reference.

Flow cytometry is a useful tool in the analysis of biomolecules. In the context of the present invention, flow cytometry is particularly useful in the analysis of microsphere based assays, such as the Luminex xMAP system. Flow cytometry involves the separation of cells or other particles, such as microspheres, in a liquid sample. Generally, the purpose of flow cytometry is to analyze the separated particles for one or more characteristics. The basic steps of flow cytometry involve the direction of a fluid sample through an apparatus such that a liquid stream passes through a sensing region. The particles should pass one at a time by the sensor and are categorized based on size, refraction, light scattering, opacity, roughness, shape, fluorescence, etc.

In the context of the Luminex xMAP system, flow cytometry can be used for simultaneous sequence identification and hybridization quantification. Internal dyes in the microspheres are detected by flow cytometry and used to identify the specific nucleic acid sequence to which a microsphere is coupled. The label on the target nucleic acid molecule is also detected by flow cytometry and used to quantify target hybridization to the microsphere.

Methods of flow cytometry are well know in the art and are described, for example, in U.S. Pat. Nos. 5,981,180; 4,284, 412; 4,989,977; 4,498,766; 5,478,722; 4,857,451; 4,774,189;

4,767,206; 4,714,682; 5,160,974; and 4,661,913, all of which are specifically incorporated by reference.

E. miRNA Isolation

As discussed above, the oxocarbonamide peptide nucleic acids of the present invention are particularly useful in the detection of small RNA molecules, such as miRNA, in a sample. miRNAs are 18-25 nucleotide (nt) RNAs that are processed from longer endogenous hairpin transcripts. The increased sensitivity and selectivity of OxoPNAs of the present invention overcome the limitations of their DNA-probe counterparts for the detection of short nucleotide targets.

Small RNA molecules may be isolated from a sample, such as a cell sample, by a variety of methods known in the art. The most commonly used method is to co-purify the miRNA with total RNA using a combination of acidified phenol and guanidine isothiocyanate using care not to remove the highly-soluble short RNA (see, e.g., Pfeffer et al., 2003). This method isolates total RNA, which comprises transfer RNA (tRNA), ribosomal RNA (rRNA), polyA messenger RNA (mRNA), short interfering RNA (siRNA), small nuclear RNA (snRNA), and microRNA (miRNA). If desired, the miRNA can be enriched from the total RNA by size selection using gel purification (Pfeffer, Id.).

Other methods for isolating miRNA include the mirVana™ miRNA Isolation Kit (Ambion). The resulting RNA preparation (less than about 200 nucleotides) is enriched for miRNAs, siRNAs, and/or snRNAs. In addition, the Absolutely RNA® Miniprep Kit (Stratagene) may be used to isolate total RNA comprising miRNA. Removal of genomic DNA is desirable as its presence in the total RNA could lead to false or misleading results.

F. Therapeutic Applications

The oxocarbonamide peptide nucleic acids of the present invention may be used as double-stranded siRNA molecules, single-stranded antisense molecules, or as decoy molecules for nucleic acid binding proteins. These uses may be for therapeutic or research purposes. Naturally occurring DNA molecules are generally not well suited to these applications due to the instability of unmodified DNA in vivo. However, chemically modified oligonucleotides have been shown to be effective inhibitors of coding and non-coding RNAs (see Weiler et al., 2006).

Oxocarbonamide peptide siRNA, antisense, or decoy molecules may be prepared by solid phase synthesis as described above. For therapeutic application it may be desirable to incorporate hydrophilic groups, such as polyethylene glycol (PEG), in to the OxoPNA in order to increase its hydrophilicity. Cationic polymers such as polyamidoamine (PMAM) dendrimers or a polyethyleneimine (PEI) may be combined with OxoPNAs for DNA delivery.

The nucleotide sequence of the siRNA or antisense molecule is defined by the nucleotide sequence of its target gene. The siRNA or antisense molecule contains a nucleotide sequence that is essentially identical to at least a portion of the target gene. Preferably, the siRNA or antisense contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine. The nucleotide sequence of the decoy molecule is defined by the recognition sequence of the target protein.

The cell containing the target gene or protein may be derived from or contained in any organism (e.g., plant, animal, protozoan, virus, bacterium, or fungus). The plant may be a monocot, dicot or gynmosperm; the animal may be a vertebrate or invertebrate. Preferred microbes are those used in agriculture or by industry, and those that a pathogenic for plants or animals. Fungi include organisms in both the mold and yeast morphologies. Examples of vertebrates include fish and mammals, including cattle, goat, pig, sheep, hamster, mouse, rat, and human; invertebrate animals include nematodes, insects, arachnids, and other arthropods. Preferably, the cell is a vertebrate cell. More preferably, the cell is a mammalian cell.

The cell having the target gene or protein may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus encompasses fetal tissue. The cell having the target gene or protein may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells, of the endocrine or exocrine glands.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence has been introduced. Therefore, recombinant cells are distinguishable from naturally occurring cells which do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, $CD34^+$ cells $CD4^+$ cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, or testes.

G. Anchor Molecules

The oxocarbonamide peptide nucleic acids of the present invention may be used as anchor molecules for the attachment of different functional molecules to DNA via specific Watson-Crick base pairing. The coupling of molecules with different biological function to plasmids or other nucleic acid molecules of interest can improve the targeting of genetic material in non-viral gene delivery systems. Coupling methods based on chemical linkage of peptides to plasmid DNA can interfere with gene expression. Thus, coupling via specific Watson-Crick base pairing provides an attractive alternative to chemical linkage. Those in the art are familiar with methods of coupling peptides and other molecules to plasmid DNA using nucleic acid analogs, such as those described for PNA, bisPNA, and LNA (see e.g., Lundin et al., 2005; Branden et al., 1999; Rebuff et al., 2002; Hertoghs et al., 2003; Branden et al., 2002).

H. Nucleic Acid Analogues for Programmable Assembly

The oxocarbonamide peptide nucleic acids of the present invention may also be used in the programmed assembly of nanoscale devices. Nucleic acid guided assembly has been used to organize gold nanoparticles (Mirkin et al., 1996; Alivisatos et al., 1996; Mucic et al., 1998), nanowires (Mbindyo et al., 2003), quantum dots (Parak et al., 2002); Mitchell et al., 1999), carbon nanotubes (Dwyer et al., 2004), dendrimers (DeMattei et al., 2004), micron-size polystyrene beads (Milam et al., 2003), virus particles (Strable et al., 2004), and to attach nano- and microparticles to substrates (Kannan et al., 2004; Hartmann et al., 2002); Niemeyer et al., 2001). The oxocarbonamide peptide nucleic acids of the present invention provide advantages in programmed assembly over natural DNA due to increased stability and greater affinity between complementary oligomers.

I. Kits

Any of the compositions described herein may be comprised in a kit. In one embodiment, the present invention provides a kit comprising one or more oxocarbonamide peptide nucleic acid molecules. In certain aspects of the invention, the kit comprises a plurality of oxocarbonamide peptide nucleic acid molecules having at least 10, 20, 30, 40, 50, 60, 70, 80, 90, 100, 150, 200, 300, 400, 500, 600, 700, 800, 900, 1000, 10000, 20000, 30000, 40000, 50000, 60000, 70000, 80000, 90000, or 100000 different nucleic acid sequences. In another embodiment of the invention, the kit may include components for making a nucleic acid array, and thus, may include, for example, a solid support. In some aspects of the invention, the kits will comprise pre-fabricated arrays, such as, for example, microspheres coupled to oxocarbonamide peptide nucleic acid probes. It may also include one or more buffers, such as hybridization buffer or a wash buffer.

The kits may comprise suitably aliquoted nucleic acid compositions of the present invention, whether labeled or unlabeled, as may be used to isolate, separate, detect, or amplify a targeted nucleic acid. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the oxocarbonamide peptide nucleic acids, and any other reagent containers in close confinement for commercial sale. Such containers may include cardboard or injection or blow-molded plastic containers into which the desired vials, bottles, etc. are retained.

When the components of the kit are provided in one or more liquid solutions, the liquid solution may be an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

A kit may also include instructions for employing the kit components. Instructions may include variations that can be implemented.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,284,412
U.S. Pat. No. 4,498,766
U.S. Pat. No. 4,661,913
U.S. Pat. No. 4,714,682
U.S. Pat. No. 4,767,206
U.S. Pat. No. 4,774,189
U.S. Pat. No. 4,857,451
U.S. Pat. No. 4,989,977
U.S. Pat. No. 5,160,974
U.S. Pat. No. 5,478,722
U.S. Pat. No. 5,539,082
U.S. Pat. No. 5,714,331
U.S. Pat. No. 5,719,262
U.S. Pat. No. 5,736,330
U.S. Pat. No. 5,736,336
U.S. Pat. No. 5,766,855
U.S. Pat. No. 5,773,571
U.S. Pat. No. 5,786,461
U.S. Pat. No. 5,837,832
U.S. Pat. No. 5,837,860
U.S. Pat. No. 5,843,663
U.S. Pat. No. 5,849,486
U.S. Pat. No. 5,851,772
U.S. Pat. No. 5,891,625
U.S. Pat. No. 5,900,481
U.S. Pat. No. 5,919,626
U.S. Pat. No. 5,981,180
U.S. Pat. No. 6,057,107
Alivisatos et al., *Nature*, 382:609-611, 1996.

Ambros et al. *RNA*, 9:277-279, 2003.
Branden et al., *Methods Enzymol.*, 346:106-124, 2002.
Branden et al., *Nat. Biotechnol.*, 17:784-787, 1999.
Calin et al., *Proc. Natl. Acad. Sci. USA*, 99:15524-15529, 2002.
DeMattei et al., *Nano Lett.*, 4:771-777, 2004.
Dwyer et al., *Nanotechnology*, 15:1240-1245, 2004.
Egholm et al., *Nature*, 365(6446):566-568, 1993.
Fire et al., *Nature*, 391:806-811, 1998.
Fujii et al., *Chem. Commun.*, 717-718, 1998.
Girault et al., *Bioconj. Chem.*, 7:445-450, 1996.
Grad et al., *Mol. Cell*, 11:1253-1263, 2003.
Grishok et al., *Cell*, 106:23-24, 2001.
Hartmann et al., *Mater. Res.*, 17:473-478, 2002.
Hertoghs et al., *Nucleic Acids Res.*, 31:5817-5830, 2003.
Holmstrom et al., *Anal. Biochem.* 209:278-283, 1993.
Howarth et al., *J. Org. Chem.*, 62:5441-5450, 1997.
Hutvagner and Zamore, *Science*, 297:2056-2060, 2002.
Kannan et al., *Nano Lett.*, 4:1521-1524, 2004.
Ke et al., *Curr. Opin. Chem. Biol.*, 7:516-523, 2003.
Koshkin and Dunford, *J. Biol. Chem.*, 273(11):6046-6049, 1998a.
Koshkin and Wengel, *J. Org. Chem.*, 63(8):2778-2781, 1998b.
Krichevsky et al., *RNA* 9:1274-1281, 2003.
Lagos-Quintana et al., *Science*, 294:853-858, 2001.
Lee and Ambros, *Science*, 294:858-862, 2001a.
Lee and Ambros, *Science*, 294:862-864, 2001b.
Lee et al., *Cell*, 75:843-854, 1993.
Lipardi et al., *Cell*, 107:297-230, 2001.
Liu et al., *Proc. Natl. Acad. Sci, USA*, 101:9740-9744, 2004.
Lundin et al., *Biomolecular Engineering*, 22:185-192, 2005.
Mbindyo et al., *Adv. Mater.*, 13:249-254, 2003.
Mc Cairn et al., *J. Combinatorial Chem.*, 8(1):1-3, 2006.
Milam et al., *Langmuir*, 19:10317-10323, 2003.
Mirkin et al., *Nature*, 382:607-609, 1996.
Mitchell et al., *J. Am. Chem. Soc.*, 121:8122-8123, 1999.
Mucic et al., *J. Am. Chem. Soc.*, 120:12674-12675, 1998.
Nelson et al., *TIBS*, 28:534-540, 2003.
Newton et al., *Nucl. Acids Res.* 21:1155-1162, 1993.
Niemeyer et al., *Colloid. Polym.*, 279:68-72, 2001.
Nykanen et al., *Cell*, 107:309-321, 2001.
Parak et al., *Chem. Mater.*, 14:2113-2119, 2002.
Paushkin et al., *Curr. Opin. Cell Biol.*, 14:305-312, 2002.
PCT Appln. PCT/EP/01219
PCT Appln. WO 92/20702
Pfeffer et al., In: *Cloning of Small RNA Molecules in Current Protocols in Molecular Biology*, Ausubel et al. (Eds), Ch. 26.4.1-26.4.18, Wiley Interscience, NY, 2003.
Porter et al., *Bioorganic Med. Chem. Ltrs.*, 12:1051-1054, 2002.
Poy et al., *Nature*, 432:226-230, 2004.
Rasmussen et al., *Anal. Biochem*, 198:138-142, 1991.
Rebuff et al., *FASEB J*, 16:1426-1428, 2002.
Reinhart et al. *Genes Dev.*, 16:1616-1626, 2002.
Reinhart et al., *Nature*, 403:901-906, 2000.
Running et al., *BioTechniques* 8:276-277, 1990.
Sato et al., *J. Am. Chem. Soc.*, 124:12715-12724, 2002.
Schmittgen et al., *Nucleic Acids Res.*, 32:e43, 2004.
Strable et al., *Nano Lett.*, 4:1385-1389, 2004.
Thomson et al., *Nature Methods*, 1:1-6, 2004.
Valoczi et al., *Nuc. Acids Res.*, 32(22):e175, 2004.
Wahlestedt et al., *Proc. Natl. Acad. Sci. USA*, 97(10):5633-5638, 2000.
Weiler et al., *Gene Therapy*, 13:496-502, 2006.
Zeng and Cullen, *RNA*, 9:112-123, 2003.
Zhang et al., *EMBO J.*, 21:5875-5885, 2002.

What is claimed is:

1. An oxocarbonamide peptide nucleic acid having the formula (II):

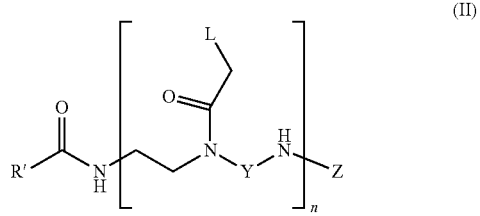

(II)

wherein:

n is an integer from 1 to 100;

each L is independently selected from the group consisting of nucleobases and DNA intercalators;

each Y is independently selected from the group consisting of $CH_2CO$, formula (IVa), formula (IVb), formula (IVc), formula (IVd), formula (IVe), formula (IVf), formula (IVg), and formula (IVh):

(IVa)

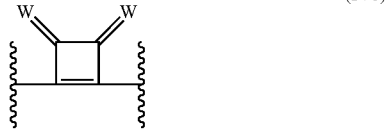

(IVb)

(IVc)

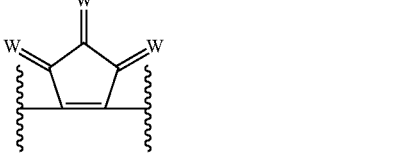

(IVd)

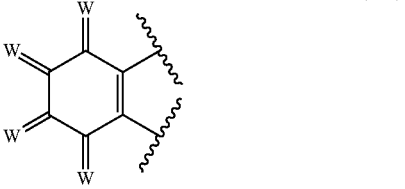

(IVg)

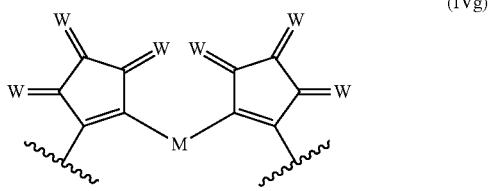

(IVh)

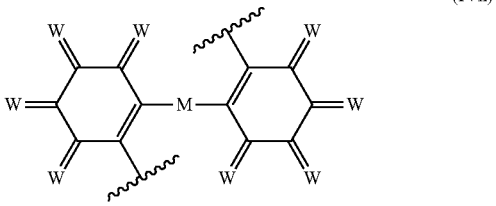

-continued

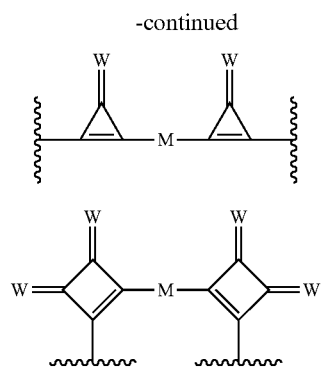

(IVe)

(IVf)

wherein each W is independently selected from the group consisting of O and S, and M is selected from the group consisting of no linker, benzene, substituted benzene, formula (IVi), and formula (IVj):

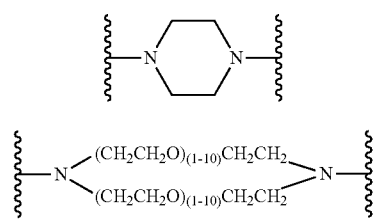

(IVi)

(IVj)

and where at least one Y is selected from the group consisting of formula (IVa), formula (IVb), formula (IVc), formula (IVd), formula (IVe), formula (IVf), formula (IVg), and formula (IVh);

R' is selected from the group consisting of hydrogen, alkyl, reporter ligands, carboxylates, esters, alcohols, carbamides, aldehydes, amines, amides, sulfur oxides, nitrogen oxides, and halides; and Z is selected from the group consisting of $CO_2H$, $NH_2$, and SH.

2. The oxocarbonamide peptide nucleic acid of claim 1, wherein n is an integer from 5 to 30.

3. The oxocarbonamide peptide nucleic acid of claim 1, wherein at least one Y is formula (IVa).

4. The oxocarbonamide peptide nucleic acid of claim 1, wherein at least one Y is formula (IVe).

5. The oxocarbonamide peptide nucleic acid of claim 1, wherein at least one Y is $CH_2CO$.

6. The oxocarbonamide peptide nucleic acid of claim 1, wherein each L is a naturally occurring nucleobase.

7. The oxocarbonamide peptide nucleic acid of claim 6, wherein the naturally occurring nucleobase is selected from the group consisting of adenine, thymine, guanine, and cytosine.

8. The oxocarbonamide peptide nucleic acid of claim 1, wherein at least one L is a non-naturally occurring nucleobase.

9. The oxocarbonamide peptide nucleic acid of claim 1, wherein the non-naturally occurring nucleobase is selected from the group consisting of bromothymine, azaadenine, and azaguanine.

10. The oxocarbonamide peptide nucleic acid of claim 1, wherein R' is an amine or amide.

11. The oxocarbonamide peptide nucleic acid of claim 1, further defined as having the formula (IIa):

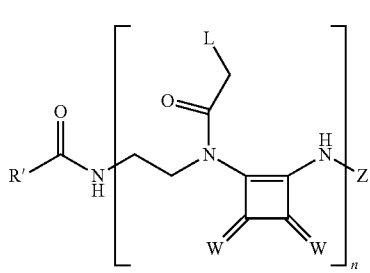

(IIa)

wherein W is O or S.

12. The oxocarbonamide peptide nucleic acid of claim 11, wherein W is O.

13. A method for detecting a target nucleic acid molecule, comprising:
  (a) providing an oxocarbonamide peptide nucleic acid of claim 1 comprising a sequence complementary to a sequence of a target nucleic acid molecule;
  (b) contacting the oxocarbonamide peptide nucleic acid with the target nucleic molecule under conditions that allow the oxocarbonamide peptide nucleic acid to hybridize with the target molecule; and
  (c) detecting the hybridization.

14. The method of claim 13, wherein the target nucleic acid molecule is a DNA molecule.

15. The method of claim 13, wherein the target nucleic acid molecule is an RNA molecule.

16. The method of claim 15, wherein the RNA molecule is an miRNA molecule.

17. The method of claim 13, wherein the oxocarbonamide peptide nucleic acid is labeled.

18. The method of claim 13, wherein the target nucleic acid molecule is labeled.

19. The method of claim 13, wherein the oxocarbonamide peptide nucleic acid is covalently attached to a solid support.

20. The method of claim 19, wherein the solid support is a microsphere.

21. The method of claim 20, wherein the microsphere is fluorescently labeled.

22. A method for detecting one or more target nucleic acid molecules in a multiplexed assay, comprising:
  (a) providing a plurality of different oxocarbonamide peptide nucleic acids of claim 1, wherein each different oxocarbonamide peptide nucleic acid is covalently attached to a defined location on an array;
  (b) contacting a sample comprising the one or more target nucleic acid molecules with the array under conditions that allow the one or more target nucleic acid molecules to hybridize to complementary oxocarbonamide peptide nucleic acids on the array; and
  (c) detecting the hybridization.

23. The method of claim 22, wherein the array comprises a plurality of microspheres.

24. The method of claim 22, wherein the one or more target nucleic acid molecules are miRNA molecules.

25. The method of claim 22, wherein the oxocarbonamide peptide nucleic acids are between about 10 and about 60 nucleobases in length.

* * * * *